United States Patent
Nakazawa et al.

(10) Patent No.: US 9,884,077 B2
(45) Date of Patent: Feb. 6, 2018

(54) EXTRACT AND PREPARATION CONTAINING SAID EXTRACT

(71) Applicant: NIPPON ZOKI PHARMACEUTICAL CO., LTD., Osaka (JP)

(72) Inventors: Yoshitaka Nakazawa, Hyogo (JP); Yoji Shibayama, Hyogo (JP); Ko Nakamura, Hyogo (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 157 days.

(21) Appl. No.: 14/787,857

(22) PCT Filed: Apr. 30, 2014

(86) PCT No.: PCT/JP2014/061959
§ 371 (c)(1),
(2) Date: Oct. 29, 2015

(87) PCT Pub. No.: WO2014/178394
PCT Pub. Date: Nov. 6, 2014

(65) Prior Publication Data
US 2016/0089402 A1   Mar. 31, 2016

(30) Foreign Application Priority Data
Apr. 30, 2013 (JP) ................. 2013-095565

(51) Int. Cl.
*A61K 35/76* (2015.01)
*A61K 35/36* (2015.01)

(52) U.S. Cl.
CPC .............. *A61K 35/36* (2013.01); *A61K 35/76* (2013.01)

(58) Field of Classification Search
None
See application file for complete search history.

(56) References Cited

U.S. PATENT DOCUMENTS

| | | | |
|---|---|---|---|
| 4,985,254 A | 1/1991 | Konishi | |
| 4,996,988 A | 3/1991 | Ohhara et al. | |
| 5,013,558 A | 5/1991 | Konishi | |
| 5,057,324 A | 10/1991 | Shibayama et al. | |
| 5,560,935 A | 10/1996 | Konishi et al. | |
| 6,051,613 A | 4/2000 | Ohno et al. | |
| 6,165,515 A | 12/2000 | Matsuyama et al. | |
| 6,306,345 B1 | 10/2001 | Bronshtein et al. | |
| 6,365,192 B1 | 4/2002 | Konishi | |
| 6,726,932 B2 | 4/2004 | Konishi | |
| 7,060,308 B2 | 6/2006 | Rajendran et al. | |
| 7,148,012 B2 | 12/2006 | Nishioka | |
| 7,238,487 B2 | 7/2007 | Nishioka | |
| 7,435,547 B2 | 10/2008 | Nishioka | |
| 8,293,280 B2 | 10/2012 | Ansari et al. | |
| 8,338,108 B2 | 12/2012 | Nakamura et al. | |
| 8,568,789 B2 | 10/2013 | Kurohashi et al. | |
| 8,900,639 B2 | 12/2014 | Cheung | |
| 2006/0051375 A1 | 3/2006 | Cheung | |
| 2006/0051376 A1 | 3/2006 | Nishioka | |
| 2006/0134139 A1 | 6/2006 | Kurohashi et al. | |
| 2006/0134646 A1 | 6/2006 | Ansari et al. | |
| 2006/0263388 A1 | 11/2006 | Nishioka | |
| 2007/0218037 A1 | 9/2007 | Nishioka | |
| 2010/0048408 A1 | 2/2010 | Naiki et al. | |
| 2011/0003009 A1 | 1/2011 | Cheung | |
| 2011/0111051 A1 | 5/2011 | Oishi et al. | |
| 2012/0135083 A1 | 5/2012 | Kurohashi et al. | |
| 2013/0028982 A1 | 1/2013 | Tamaki | |
| 2013/0122512 A1 | 5/2013 | Mutoh et al. | |
| 2013/0183386 A1 | 7/2013 | Cheung | |
| 2014/0017311 A1 | 1/2014 | Kurohashi et al. | |
| 2015/0265665 A1 | 9/2015 | Moshtagh | |

FOREIGN PATENT DOCUMENTS

| | | |
|---|---|---|
| CN | 1205233 | 1/1999 |
| CN | 1237632 A | 12/1999 |
| CN | 1613305 | 5/2005 |

(Continued)

OTHER PUBLICATIONS

Kudo et al, Antinociceptive effects of neurotropin in a rat model of central neuropathic pain: DSP-4 induced noradrenergic lesion. Neuroscience letters, (Sep. 26, 2011) vol. 503, No. 1, pp. 20-22.*
"Folia Pharmacologica Japonica", vol. 72, No. 5, 1976, pp. 573-584.
Iyakuhin Tenpu Bunsho, "Neurotropin-jo 4 Tan'i", 7th Edition, Feb. 2012, with English Translation.
Iyakuhin Tenpu Bunsho, "Neurotropin Chushaeki 1.2 Tan'i", 8th Edition, Feb. 2012, with English Translation.
C.H. Jen et al., "A competitive binding study of chemokine, sulfated receptor, and glycosaminoglycan interactions by nano-electrospray ionization mass spectrometry", Anal. Biochem., vol. 407, No. 1, 2010, pp. 134-140.
Huang et al., "Tyrosine sulphation of sphingosine 1-phosphatel (S1P$_1$) is required for S1P-mediated cell migration in primary cultures of human umbilical vein endothelial cells", J. Biochem., vol. 146, No. 6, 2009, pp. 815-820.

(Continued)

*Primary Examiner* — Qiuwen Mi
(74) *Attorney, Agent, or Firm* — Greenblum & Bernstein, P.L.C.

(57) ABSTRACT

An extract from inflamed skins of rabbits inoculated with vaccinia virus is provided where the quality of the extract is more stabilized. A preparation, etc. containing said extract as an active ingredient is also provided. When the amount of sulfated tyrosine contained in an extract from inflamed skins of rabbits inoculated with vaccinia virus and also contained in a preparation containing said extract as an active ingredient is used as an index, the quality of the extract and the preparation among the manufacturing lots can be warranted as a more stabilized one. In the extract from inflamed skins of rabbits inoculated with vaccinia virus and the preparation containing said extract where the quality thereof is more stabilized by such a method, the efficacy and the safety thereof are now guaranteed more strictly resulting in very high usefulness.

21 Claims, No Drawings

(56) References Cited

FOREIGN PATENT DOCUMENTS

| | | |
|---|---|---|
| EP | 0300973 | 1/1989 |
| EP | 0315591 | 5/1989 |
| EP | 0341209 | 11/1989 |
| EP | 0348353 | 12/1989 |
| EP | 0645142 | 3/1995 |
| EP | 0919238 | 6/1999 |
| EP | 0953352 | 11/1999 |
| EP | 1557171 | 7/2005 |
| EP | 1566178 | 8/2005 |
| EP | 2 191 836 | 6/2010 |
| GB | 697351 | 9/1953 |
| JP | 53-101515 | 9/1978 |
| JP | 55-87724 | 7/1980 |
| JP | 57-77697 | 5/1982 |
| JP | 58-35117 | 3/1983 |
| JP | 1-265028 | 10/1989 |
| JP | 1-319422 | 12/1989 |
| JP | 2-28119 | 1/1990 |
| JP | 07/097336 | 4/1995 |
| JP | 8-291077 | 11/1996 |
| JP | 2594222 | 12/1996 |
| JP | 10-194978 | 7/1998 |
| JP | 11-80005 | 3/1999 |
| JP | 11-139977 | 5/1999 |
| JP | 2000-16942 | 1/2000 |
| JP | 2000-336034 | 12/2000 |
| JP | 3818657 | 6/2006 |
| JP | 2004-300146 | 10/2008 |
| JP | 4883798 | 2/2012 |
| WO | 2004/039383 | 5/2004 |
| WO | 2004/060381 | 7/2004 |
| WO | WO06065947 | 6/2006 |
| WO | 2009/028605 | 3/2009 |
| WO | 2011/162317 | 12/2011 |
| WO | 2012-051173 | 4/2012 |
| WO | 2014/057995 | 4/2014 |

OTHER PUBLICATIONS

International Preliminary Report on Patentability of International Application No. PCT/JP2014/061959, dated Nov. 3, 2015.
"Drugs in Japan, Ethical Drugs", Japan Pharmaceutical Information Center, 1994, pp. 1434-1435.
Toyomaki et al., "Study on the in vitro Assay Method in Evaluating the Inhibiting Effect of various Drugs on the Production of Plasma Kallikrein-Like Activity", Kiso to Rinsho (The Clinical Report), vol. 20, No. 17, 8889-8895 (1986).
Extended European Search Report in respect to European Application No. 14791811.4, dated Nov. 8, 2016.
Katsuhiro Toda et al, "Antinociceptive effects of neurotropin in a rat model of painful peripheral mononeuropathy," Life Sciences, Pergamon Press, Oxford, GB, vol. 62, No. 10, Jan. 30, 1998, pp. 913-921, XP002592902.
Takashi Kudo et al., "Antinociceptive effects of neurotropin in a rat model of central neuropathic pain: DSP-4 induced noradrenergic lesion", Neuroscience Letters, Limerick, IE, vol. 503, No. 1, Jul. 30, 2011, pp. 20-22, XP028287906.
XP002763443, Database WPI Thomson Scientific, London, GB, Nov. 24, 2011.
XP002763444, Database WPI Thomson Scientific, London, GB, Sep. 30, 1994.

* cited by examiner

EXTRACT AND PREPARATION CONTAINING SAID EXTRACT

TECHNICAL FIELD

The present invention relates to an extract from inflamed skins of rabbits inoculated with vaccinia virus wherein the quality is more stabilized by confirming by such a means of tests or inspections that it contains a predetermined amount of sulfated tyrosine and also to a preparation, etc. In which the extract is an active ingredient.

BACKGROUND ART

Drug is approved for its manufacture and distribution only after its quality is warranted. In Japan, that is stipulated in Article 14 of the Pharmaceutical Affairs Law. In view of the characteristics of a drug, such a management is basically same in other countries as well. The reason why warranty of the quality is important for a drug as such is that the quality guarantees efficacy and safety of a drug. Conversely, with regard to a drug for which no quality is warranted, neither efficacy nor safety is guaranteed therefore whereby such a one is not competent as a drug.

In Japan, a material substance being used for the production of a drug and able to be an active ingredient of a drug is called a "drug substance" The same as in a drug, a drug substance is also necessary that its quality is warranted. That is because the quality of a drug depends upon the quality of a drug substance. Incidentally, according to Japanese laws and regulations related to pharmaceutical affairs, a drug substance is stipulated as a drug which is exclusively used for the manufacture of other drug and, in terms of the definition therefore, a drug substance is covered by a drug. However, in the present application, a medicament and a drug substance may be sometimes separately referred to for the sake of convenience and, in such a case, the meaning of a drug shall exclude a drug substance.

It is general that, when a drug or a drug substance is manufactured by a predetermined manufacturing method, that having a predetermined quality is manufactured. Accordingly, in order to maintain the quality of a drug or a drug substance, manufacture control is also important. For such a purpose, there has been stipulated "Ministerial Ordinance concerning the Standards for Manufacture Control and Quality Control of Drugs and Quasi-Drugs" in Japan. This ministerial ordinance is called GMP (abbreviation of Good Manufacturing Practice) in Japan as well. In GMP, "manufacture control" and "quality control" of drugs, etc. are stipulated. In "manufacture control", there is adopted such a way of thinking that the quality is maintained by controlling the material preparation and the manufacturing steps from the initial to the final stages thereof. "Quality control" has been mainly conducted by means of confirmation of the tests and inspections conducted after the manufacture whether the manufactured drug or drug substance actually has predetermined quality standards. When the result of the tests and inspections does not satisfy the previously stipulated standards, then shipment, distribution, use, etc. of the drug and drug substance are not allowed. As such, the quality of drugs and drug substances are controlled by means of the manufacture control and the quality control.

An extract from inflamed skins of rabbits inoculated with vaccinia virus (hereinafter, it will be sometimes referred to as "the present extract") is an extract containing a non-proteinous active substance extracted and separated from the inflamed skin tissues of rabbits by the inoculation of vaccinia virus. Although the present extract is liquid in an extracted state, it is also possible to make into a solid by means of drying.

As will be mentioned later, a preparation containing the present extract as an active ingredient (hereinafter, it will be sometimes called "the present preparation") is very useful as a drug. Since the present extract is an active ingredient of the present preparation in that case, the present extract is a drug substance of the present preparation. In a specific product as the present preparation which is manufactured and distributed by the applicant, there is "a preparation containing an extract from inflamed skins of rabbits inoculated with vaccinia virus" (trade name: NEUROTROPIN [registered trademark]; hereinafter, it will be referred to as "NTP preparation"). In NTP preparation, there are injection (hereinafter, it will be referred to as "NTP injection") and tablet (hereinafter, it will be referred to as "NTP tablet") and both belong to an ethical drug. An extract from inflamed skins of rabbits inoculated with vaccinia virus (hereinafter, it will be referred to as "NTP extract") which is an active ingredient of NTP preparation is a drug substance of NTP preparation. NTP extract is covered by the present extract while NTP preparation (NTP injection and NTP tablet) is covered by the present preparation.

Indications of NTP injection are "low back pain, cervicobrachial syndrome, symptomatic neuralgia, itchiness accompanied by skin diseases (eczema, dermatitis, urticaria), allergic rhinitis and sequelae of subacute myelo-optico-neuropathy (SMON) such as coldness, paresthesia and pain". Indications of NTP tablet are "postherpetic neuralgia, low back pain, cervicobrachial syndrome, periarthritis scapulohumeralis and osteoarthritis". NTP preparation has been created and developed as a drug by the applicant. NTP preparation has been appreciated for its excellent advantage for efficacy and safety, sold for many years and established a firm position in the Japanese pharmaceutical market. At present, NTP preparation is being exported to China and sold under a trade name of "神経妥楽平/NEUROTROPIN". Indications of NTP preparation in China are the same as those in Japan.

As such, the present preparation is very useful as a drug and the present extract is also very useful as a drug substance for the present preparation. However, as mentioned already, the present extract is extracted and separated from the inflamed skin tissues of rabbits by the inoculation of vaccinia virus. Therefore, the present extract contains quite a lot of substances (components) and the present preparation manufactured using the present extract also contains quite a lot of substances (components). Accordingly, it is a very important matter how to control the quality of the present extract and the present preparation in a stable one.

Many of drugs are the preparations containing one or two to three substances (components) at the largest as an active ingredient and, usually, such substances are the chemically synthesized compounds. Therefore, when the content of the compound(s) in said preparation is measured and a predetermined content is contained, the quality of said preparation in view of the content of the active ingredient(s) is guaranteed. However, the present extract is an extract from inflamed skin tissues of rabbits by the inoculation of vaccinia virus and contains quite many kinds of substances. It goes without saying that the present preparation where the present extract is an active ingredient also contains quite many kinds of substances. Thus, in the present extract and the present preparation, specific one or several kind(s) of substance(s) is/are not the active ingredient(s) as such whereby it is not possible to conduct a quality control as in the case of conventional drug where active ingredient(s) is/are specified as substance(s). Therefore, quantitative determination for active ingredient(s) of the present extract and the present preparation manufactured by the applicant or of NTP extract and NTP preparation is being carried out by such a method where the biological activity (titer) thereof is measured.

Said method is a biological test method where an analgesic coefficient is determined using SART-stressed (repeated cold stressed) animals which are chronic stressed animals showing a lowered pain threshold than normal animals (*Folia Pharmaclogica Japonica*, vol. 72, no. 5, pages 573 to 584, 1976). In accordance with the method in this literature, the analgesic coefficient is determined by conducting an analgesic test according to a Randall-Selitto method using SART-stressed (repeated cold stressed) animals which are chronic stressed animals showing a lowered pain threshold than normal animals. In this method, an analgesic effect is measured using a pressure weight as an index where the pressure stimulation is applied to the tail of mouse and the mouse shows an escape reaction. An analgesic coefficient is a value where the pressure weight measured after administration of a drug is divided by the value before the administration. In NTP extract and NTP preparation, the case where an analgesic coefficient showed more than a predetermined value defined by the applicant is judged to be positive for an analgesic effect and the rate of the numbers of animals judged to be positive is determined and used as an analgesic efficacy rate (%). This value is used and $ED_{50}$ value is determined from the result upon measurement of standard preparation diluted to various concentrations. "Neurotropin Unit (NU)" which is a unit of biological activity (titer) using for NTP preparation by the applicant is defined that the activity of 1 mg of the present extract where the $ED_{50}$ value is the dose of 100 mg/kg is 1 Neurotropin unit. $ED_{50}$ value for each NTP preparation is measured and compared with that of the standard preparation whereupon an analgesic activity (active ingredient content) is quantitatively determined. Hereinafter in the present application, the word "unit" is used as a measure of the active ingredient content (titer) of the present extract and the present preparation and it is substantially in the same meaning as "Neurotropin Unit" used for NTP extract and NTP preparation.

In the meanwhile, it is stipulated that the present extract and the present preparation or NTP extract and NTP preparation manufactured by the applicant are to be subjected to the following plural identity tests in addition to the abovementioned quantification of the analgesic activity and should conform to them. Thus, with regard to the present extract and the present preparation manufactured by the applicant, not only the above-mentioned biological activity (titer) is used for guaranteeing the appropriateness of the manufactured lots but also the following plural identity tests are carried out and adaptation thereto is used as a necessary condition for use and shipment of the present extract and the present preparation.

Identity test of amino acids by a liquid chromatographic method

Identity test of ultraviolet absorbing substances by Ultraviolet-visible Spectrophotometry Identity test of phosphorus by a color reaction method Identity test of nucleic acid base by a liquid chromatographic method Identity test of inhibitory action for the production of kallikrein-like substance by an in vitro test method However, even when such tests are carried out, it is not always true that the amino acids, ultraviolet absorbing substances, phosphorus, nucleic acid bases, etc. which are objects of the tests are the crucial active ingredients of the present extract and the present preparation. Moreover, in those tests, the identity test for amino acids, ultraviolet absorbing substances, phosphorus and nucleic acid bases is a qualitative test which merely confirms the presence of amino acids, etc. which are objects of the tests and does not check how much amount is contained therein. Even under such circumstances however, those tests are still obligatory for the applicant in order to receive an approval for the manufacture of drugs from the government as a means for reducing the variations in the quality among the manufacturing lots and for guaranteeing the uniform quality in both of the present extract and the present preparation where the active ingredients are unidentified.

Generally speaking, it is advantageous for persons who manufacture an extract from living organisms such as animals and plants or a preparation containing said extract as an active ingredient if and when the standards to which said preparation should conform are small in numbers since time, labor and cost for the test and the inspection are saved and possibility where the manufactured product does not conform to the standard is low. However, in view of guaranteeing the quality of the above extract and preparation, it is desirable that the standard as such is stipulated more strictly. Under such circumstances, the applicant has extensively investigated the new appropriate standard to which the present extract and the present preparation manufactured by the applicant should conform whereupon the present invention has been achieved. Thus, the amount of sulfated tyrosine contained in the present extract and the present preparation is measured and, when the amount is within a predetermined range, it is treated that the present extract and the present preparation as such are appropriately manufactured or, in other words, their use and shipment are permitted. As a result, the variations among manufacturing lots of the present extract and the present preparation are further reduced and the quality thereof becomes more stable. Further, as a result, efficacy and safety of the present extract and the present preparation are guaranteed more strictly. If and when there is the present extract or the present preparation wherein the amount of sulfated tyrosine is out of the stipulated range, it is treated as an adulterated product (a substandard product) whereby it is possible to control the quality of the present extract and the present preparation in a more stable manner. Thus, it is now possible to stipulate an autonomous or a public standard concerning the amount of sulfated tyrosine contained in the present extract or the present preparation. In the meanwhile, the applicant has not stipulated a standard for the amount of sulfated tyrosine contained in an NTP extract and an NTP preparation manufactured up to now and has not conducted such an act that the amount is measured and that, after confirming the measured amount is within a predetermined range, the corresponding NTP extract and NTP preparation are used, shipped, etc.

As to the documents which disclose the present extract or the present preparation, Patent Documents 1 to 3 are available. Those documents disclose the content of amino acids and nucleic acid bases in the present extract or the present preparation. Further, with regard to the present extract or the present preparation, there is a disclosure for the content of silicons in Patent Document 4. However, in those Patent Documents 1 to 4, there is no disclosure at all how much a specific substance which is sulfated tyrosine is contained in the present extract or the present preparation. It further goes without saying that, in those documents, there is neither disclosure nor suggestion at all to adopt the content of sulfated tyrosine in the present extract or the present preparation as an index for the quality control of the present extract or the present preparation in more a stable manner.

PRIOR ART DOCUMENTS

Patent Documents

Patent Document 1: Chinese Patent Laid-Open No. CN 1205233A
Patent Document 2: International Publication No. WO 2004/060381
Patent Document 3: Chinese Patent Laid-Open No. CN 1613305A
Patent Document 4: Japanese Patent Laid-Open No. Patent 07/097336

SUMMARY OF THE INVENTION

Problems to be Solved by the Invention

As mentioned above, no single substance is identified as an active ingredient in the present extract and the present preparation. Therefore, quality of the present extract and the present preparation is guaranteed by a titer test according to a biological test determining the analgesic coefficient using SART-stressed mice, plural identity tests, etc. Even by the means as such, it is still unavoidable that various components contained in the present extract and the present preparation permissibly vary for each manufacturing lot. However, since the present preparation is used as a drug for treating the diseases, it is desirable that the quality thereof is to be as constant as possible. It is very meaningful that the quality of the present extract and the present preparation is warranted to be more stable since it makes efficacy and safety of the present extract and the present preparation more constant.

Means for Solving the Problems

The present invention is to warrant the quality of the present extract and the present preparation using the amount of sulfated tyrosine contained in the present extract and the present preparation as an index. Thus, based on the above, the present invention is to provide the present extract, the present preparation, etc. which are surely manufactured in an appropriate manner by means of confirmation of containing a stipulated amount of sulfated tyrosine.

Advantages of the Invention

The present extract and the present preparation in accordance with the present invention are such ones which contain predetermined amounts of sulfated tyrosine. As a result thereof, it is possible to treat that the present extract and the present preparation in accordance with the present invention are appropriately manufactured. The present invention contributes in such a matter that the quality of the present extract and the present preparation is warranted in a more stable manner and efficacy and safety of the present extract and the present preparation become more constant.

MODE FOR CARRYING OUT THE INVENTION

Protein plays an important role in a living body. The sequence information for amino acids constituting a protein is coded in genomic DNA. After mRNA is synthesized using DNA as a template, protein is synthesized by combination of amino acids based on the information of the mRNA (Translation). Although some of the protein synthesized as such functions as it is, the case where activation is expressed or controlled by means of addition of sugar or of partial cleavage, phosphorylation, etc. after the translation is also abundant (Post-translational modification). Tyrosine sulfation is one of the modes of the post-translational modification of protein and a sulfo group is added to a tyrosine residue of protein. Sulfated tyrosine is produced during the process of metabolism of the protein being subjected to a tyrosine sulfation and is a very stable substance which is not so easily decomposed by mammalian sulfatase.

In the meanwhile, when inflammation reaction or the like is induced in a living body, there is observed a phenomenon (leucocyte rolling) in which leucocytes roll on vascular endothelia around the tissues thereof. Leucocytes conduct a repeated contact to endothelial cells by an adhesive molecule such as selectin existing on the surface thereof and search a chemotactic factor such as chemokine presented onto the vascular endothelia. When the leucocyte recognizes chemokine, it strongly adheres to vascular endothelial cells and ceases from its movement. Then the leucocyte locally destroys the junction of the endothelial cells and, from the gaps resulted thereby, it infiltrates into inflammatory tissues. Adhesion of leucocyte to vascular endothelial cells through the intermediation of selectin induces the leucocyte rolling as such and it has become clear that the tyrosine sulfation participates in this adhesion reaction. Thus, it has been shown that a sulfating modification of tyrosine near the amino terminal of PSGL-1 (P-selectin glycoprotein ligand-1) which is a receptor for selectin is essential for the binding of selectin due to its high affinity to PSGL-1. Moreover, a chemokine receptor (such as CCR5 or CXCR4) which is a G protein conjugation type receptor existing on the surface of leucocyte is also subjected to a post-translational modification due to the tyrosine sulfation. Since inflammation and tyrosine sulfation are closely related as such, it is possible to utilize a sulfated tyrosine originated from various kinds of proteins sulfated in the inflammation tissues as an index for the inflamed state of skin tissues. The present extract is extracted from the skin tissues where inflammation is resulted by inoculation of vaccinia virus to rabbits whereby it is necessary to induce a sufficient inflammation reaction. Accordingly, sulfated tyrosine is a rational substance (ingredient) as an index for controlling the quality of the present extract and of the present preparation more stably. Thus, when it is assured that the quantity of sulfated tyrosine contained in the present extract or the present preparation is in a predetermined amount or more or within a predetermined range, it is supported that various ingredients including an active ingredient derived from inflamed skin tissues of rabbits contained in the present extract or in the present preparation are stable. In the meanwhile, it has been confirmed already that no analgesic effect or the like is available in an extract which is extracted from the skins of normal rabbits by the same method as that for the present extract.

Next, a method for manufacturing the present extract and the present preparation will be illustrated.

The present extract can be prepared by such a manner that inflamed skin tissues of rabbits by the inoculation of vaccinia virus are collected, crushed and processed by adding an extraction solvent thereto, tissue fragments are removed therefrom, a treatment for removal of protein (deproteinization) is carried out, the resulting one is adsorbed with an adsorbent under an acidic condition and then an active ingredient is eluted under a basic condition therefrom.

Vaccinia virus used herein may be in any strain. Examples thereof include Lister strain, Dairen strain, Ikeda strain, EM-63 strain and New York City Board of Health strain.

With regard to a rabbit, any rabbit may be used so far as it belongs to *Lagomorpha*. Examples thereof include *Oyctolagus cuniculus*, domestic rabbit (domesticated *Olyctolagus cuniculus*), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

As to basic extracting steps for the present extract, the following steps are used for example.

(A) Inflamed skin tissues of rabbits by the intradermal inoculation with vaccinia virus are collected, and the inflamed tissues are crushed. To the crushed tissues an extraction solvent such as water, phenol water, physiological saline or phenol-added glycerin water is added to conduct an extracting treatment for several days. Then, the mixture is filtrated or centrifuged to give a crude extract (filtrate or supernatant) wherefrom tissue fragments are removed.

(B) The crude extract obtained in (A) is adjusted to acidic pH, heated and then filtered or centrifuged to conduct a deproteinizing treatment. After that, the deproteinized solution is adjusted to basic pH, heated and then filtered or centrifuged to give a deproteinized filtrate or supernatant.

(C) The filtrate or the supernatant obtained in (B) is adjusted to acidic pH and adsorbed with an adsorbent such as activated carbon or kaolin.

(D) An extraction solvent such as water is added to the adsorbent obtained in (C), the mixture is adjusted to basic pH and the adsorbed component is eluted to give an extract from inflamed skins of rabbits inoculated with vaccinia virus (the present extract).

The above is the basic steps and each of the steps will be more specifically illustrated as follows.

About (A):

The inflamed skin tissues of rabbits by the intradermal inoculation of vaccinia virus are collected. The collected skin tissues are washed and disinfected using a phenol solution, etc. This inflamed skin tissues are crushed and an extraction solvent in 1- to 5-fold thereof by volume is added thereto. Here, the term "crush" means to finely break down into minces using a mincing machine or the like. As to the extraction solvent, there may be used distilled water, physiological saline, weakly acidic to weakly basic buffer, etc. and bactericidal/antiseptic agent such as phenol, stabilizer such as glycerin, salts such as sodium chloride, potassium chloride or magnesium chloride, etc. may be appropriately added thereto. At that time, it is also possible that the cell tissue is destroyed by a treatment such as freezing/melting, ultrasonic wave, cell membrane dissolving enzyme or surfactant so as to make the extraction easier. The resulting suspension is allowed to stand for 5 to 12 days. During that period, the suspension may be heated at 30 to 45° C. with or without appropriate stirring. The resulting liquid is subjected to a treatment for separating into solid and liquid (filtered or centrifuged, etc.) to remove the tissue fragments whereupon a crude extract (filtrate or supernatant) is obtained.

About (B)

The crude extract obtained in (A) is subjected to a deproteinizing treatment. The deproteinization may be carried out by a known method which has been usually conducted and a method such as heating treatment, treatment with a protein denaturant (such as acid, base, urea, guanidine or an organic solvent including acetone), isoelectric precipitation or salting-out may be applied. After that, a common method for the removal of insoluble matters such as filtration using filter paper (such as cellulose or nitrocellulose), glass filter, Celite or Seitz filter, ultrafiltration or centrifugation is conducted to give a filtrate or a supernatant wherefrom the separated insoluble protein is removed.

About (C)

The filtrate or supernatant obtained in (B) is adjusted to acidic or, preferably, to pH 3.5 to 5.5 to conduct an operation of adsorbing with an adsorbent. Examples of the usable adsorbent include activated carbon and kaolin. An adsorbent is added to the extract followed by stirring or the extract is passed through a column filled with an adsorbent so that the active ingredient can be adsorbed with the adsorbent. When an adsorbent is added to the extract, the adsorbent with which the active ingredient is adsorbed can be obtained by means of filtration, centrifugation, etc. to remove the solution.

About (D)

For elution (desorption) of the active ingredient from the adsorbent obtained in (C), an elution solvent is added to said adsorbent and adjusted to basic or, preferably, to pH 9 to 12, elution is conducted at room temperature or with suitable heating, or with stirring, and then the adsorbent is removed by a common method such as filtration or centrifugation. As to the extraction solvent used therefore, there may be used a basic solvent such as water, methanol, ethanol, isopropanol or the like adjusted to basic pH or an appropriate mixed solvent thereof and preferably, water adjusted to pH 9 to 12 may be used. Amount of the extracting solvent may be appropriately set. In order to use the eluate obtained as such as a drug substance, the pH is appropriately adjusted to nearly neutral or the like whereby an extract from inflamed skins of rabbits inoculated with vaccinia virus (the present extract) can be finally obtained.

Since the present extract is liquid at the stage of being prepared, it is also possible that said extract is appropriately concentrated or diluted to make into a desired concentration. When a preparation is manufactured from the present extract, it is preferred to apply a sterilizing treatment with heating. For making into an injectable preparation, it is possible to add sodium chloride or the like so as to prepare a solution being isotonic to physiological saline. It is also possible that the present extract in a liquid state is subjected to an appropriate operation such as concentration to dryness whereby a solid preparation for oral administration such as tablet is manufactured. Specific methods for the manufacture of solid preparation for oral administration from the present extract are disclosed in the specifications of Japanese Patent Nos. 3,818,657 and 4,883,798. The present preparation includes an injectable preparation, a solid preparation for oral administration, etc. prepared as such.

The content of sulfated tyrosine in the present extract and the present preparation can be measured by the usual quantifying method. To be more specific, there may be used, for example, a measuring method using liquid chromatograph mass spectrometer (LC-MS) or capillary electrophoretic mass spectrometer (CE-MS) and high performance liquid chromatography (HPLC). In any of those methods, sulfated tyrosine in the present extract and the present preparation can be quantified using a calibration curve prepared by a sulfated tyrosine specimen for calibration.

The content of sulfated tyrosine contained in the present extract and the present preparation manufactured by the applicant was measured by the above methods. As a result, although there were some scatters, the present extract and the present preparation contained 125 ng or more of sulfated tyrosine per unit. To be more specific, the present extract and the present preparation contained 125 to 425 ng of sulfated tyrosine per unit. Accordingly, when quality of the present extract and the present preparation is controlled using the content of sulfated tyrosine in the present extract and the present preparation as an index, it was judged to be possible to adopt the content as such as a standard. In the meanwhile, when the variations happened in the method for the manufacture of the present extract and the present preparation, the applicant confirmed that the content of sulfated tyrosine per unit may be lower than 125 ng.

As will be apparent from the above-mentioned explanation, the term "per unit" used herein means per the content of the active ingredient in the present extract and the present preparation. The present extract (NTP extract) manufactured by the applicant contains 1.2 units/mL of the active ingredient. The present preparation for injection (NTP injection) manufactured using the same also contains 1.2 unit/mL of the active ingredient. In NTP injection, the injection where the volume is 3 mL and 1 mL are available. Accordingly, a preparation of 3 mL contains 3.6 units of the active ingredient and a preparation of 1 mL contains 1.2 units of the active ingredient. On the other hand, the present preparation for oral administration (NTP tablet) manufactured by the applicant contains 4 units of the active ingredient per tablet.

Incidentally, the present extract may be concentrated or diluted. Further, the present preparation containing various units may be also manufactured. In such cases, the amount of the active ingredient contained in a unit amount (such as per mL, per mg, per ampoule, per tablet, etc.) of the present extract and the present preparation may also vary. Therefore, it is basically meaningful that the content of sulfated tyrosine is stipulated in relation to the amount of the active ingredient of the present extract and the present preparation. That is because such a thing is connected to the relation to efficacy and safety of the present extract or the present preparation. Accordingly, the applicant stipulated the content of sulfated tyrosine in the present extract and the present preparation in terms of "per the content of the active ingredient" ("per unit"). On the other hand, since the applicant actually manufactures and distributes NTP preparation, it is also certainly meaningful to stipulate per mL or per ampoule of the specific injection or to stipulate per tablet in relation to the dose whereby such stipulation was also adopted.

In the meanwhile, in NTP injection, there are generic drugs or similar drugs (hereinafter, they will be referred to as "other company's injections") manufactured by the companies other than the applicant's company (hereinafter, they will be referred to as "other companies") in Japan and in China. For other company's injections, an extract from inflamed skins of rabbits inoculated with vaccinia virus (the present extract) which is an active ingredient is also quantitatively determined by using its analgesic effect as an index using SART stress mice. In terms of the indication, the content of the active ingredient in other company's injections is merely mentioned as "unit" in plural other company's injections in Japan which are "ROSEMORGEN Inj." (registered trademark), "NABUTOPIN Inj." (registered trademark) and "NOLPORT Inj." (registered trademark), or is mentioned as "Analgecine unit" or "AGC unit" in one other company's injection in China which is "恩再適/AN-ALGECINE" (registered trademark). However, the same as NTP injection, in any of said preparations, the content of the active ingredient is 1.2 units or 1.2 Analgecine (1.2 AGC) units per mL or 3.6 units or 3.6 Analgecine (3.6 AGC) units per ample of 3 mL preparation. To sum up, the "Neurotropin unit" used by NTP preparation and the "unit" or "Analgecine unit" used by other companies are the same measure for stipulating the content of the active ingredient, and they are different just in terms of the expression. Under such circumstances, "unit" is used in the present application in expressing the content of the present extract which is an active ingredient not only for NTP preparation but also for all other company's injections. As such, where the amount of an extract from inflamed skins of rabbits inoculated with vaccinia virus which is an active ingredient is expressed by using "unit" in plural preparations. Therefore, with regard to said preparations, the expression in terms of "unit" is clear for persons skilled in the art.

As will be apparent from the above, "the present preparation" in the present application is a conception including NTP preparation (NTP injection and NTP tablet) and other company's injections. When other companies will manufacture and distribute tablets (hereinafter, it will be referred to as "other company's tablets") as generic drug or similar drug for NTP tablet in future, the above conception also covers other company's tablets as such.

As hereunder, specific examples for the manufacture of the present extract and the present preparation and for the result of measurement of the content of sulfated tyrosine in the present extract and the present preparation are shown as Examples although the present invention is not limited at all by the description of those Examples.

EXAMPLES

Example 1 (Manufacture of the Present Extract)

Skins of healthy adult rabbits were inoculated with vaccinia virus intradermally and the inflamed skins were cut and collected. The collected skins were washed and disinfected by a phenol solution, an excessive phenol solution was removed and the residue was crushed. A phenol solution was added thereto and mixed therewith and the mixture was allowed to stand for 3 to 7 days, and further heated at 35 to 40° C. together with stirring for 3 to 4 days. After that, an extracted solution obtained by a solid-liquid separation was adjusted to pH 4.5 to 5.2 with hydrochloric acid, heated at 90 to 100° C. for 30 minutes and filtered to remove protein. The filtrate was adjusted to pH 9.0 to 9.5 with sodium hydroxide, heated at 90 to 100° C. for 15 minutes and subjected to a solid-liquid separation.

The resulting deproteinized solution was adjusted to pH 4.0 to 4.3 with hydrochloric acid, activated carbon in an amount of 2% to the mass of the deproteinized solution was added thereto and the mixture was stirred for 2 hours and subjected to the solid-liquid separation. Water was added to the collected activated carbon followed by adjusting to pH 9.5 to 10 with sodium hydroxide and the mixture was stirred at 60° C. for 90 to 100 minutes and centrifuged to give a supernatant. Water was added again to the activated carbon precipitated upon the centrifugation followed by adjusting to pH 10.5 to 11 with sodium hydroxide and the mixture was stirred at 60° C. for 90 to 100 minutes and centrifuged to give a supernatant. Both supernatants were combined and neutralized with hydrochloric acid to give the present extract.

Example 2 (Method for Measuring the Content of Sulfated Tyrosine)

The content of sulfated tyrosine in the present extract and the present preparation was measured as follows using a high-performance liquid chromatographic mass spectrometer (LC-MS).

The present extract (1.2 units/mL) manufactured according to Example 1 was diluted with water to an extent of 10-fold and injected into the LC-MS.

The present preparation (NTP injection) manufactured using the present extract which was manufactured according to Example 1 was also diluted with water to an extent of 10-fold and injected into the LC-MS.

With regard to the present preparation (NTP tablet) manufactured using the present extract which was manufactured according to Example 1, three tablets thereof were washed with 3 mL of methanol/chloroform (1:1) for three times to remove the film coat layer, dried, suspended in 12 mL of water (1 unit/mL). After centrifugation of the suspension, the supernatant was diluted with water to an extent of 10-fold and injected into the LC-MS.

With regard to sulfated tyrosine, a standard solution in an aqueous solution was prepared and a calibration curve was produced.

In the LC-MS, the 1100 Series manufactured by Agilent Technologies, Inc. and API 3000 (manufactured by Applied Biosystems/MDS Sciex) were used for an HPLC part and a mass spectroscope, respectively. Analytical conditions are as follows.

Column: Inertsil ODS-3 (ø 2.1×150 mm)
Column temperature: 25° C.; flow rate: 200 μL/minute
Mobile phase: methanol/0.05% formic acid
Methanol %/minute: 0/0-0/1-44/8-100/8.1-100/11
Injection amount: 5 μL; temperature set for the sample chamber: 4° C.
Detection: positive ion detecting MRM
Measuring conditions for the LC-MS are shown in Table 1. Each parameter in Table 1 means as follows.
DP: voltage applied to orifice plate
FP: voltage applied to focus ring
CE: collision energy
CXP: voltage applied to the outlet of Q2
NEB: pressure of nebulizer gas
a CUR: pressure of curtain gas
IS: voltage of ion spray
CAD: pressure of collision gas
TEM: turbo gas temperature

TABLE 1

| Detected Ion (Q1/Q3) | DP | FP | CE | CXP | NEB | CUR | IS | CAD | TEM |
|---|---|---|---|---|---|---|---|---|---|
| 310/274 | 20 | 100 | 20 | 20 | 12 | 10 | 5000 | 8 | 450 |

Example 3 (Measured Result of the Content of Sulfated Tyrosine in the Present Extract)

Result of measurement of the content of sulfated tyrosine in the present extract by the method mentioned in Example 2 is shown in Table 2. Content of the active ingredient in the present extract is 1.2 units/mL. The content of sulfated tyrosine in the present extract is expressed in both terms of per unit of the present extract ("/unit") and per mL of the present extract ("/mL"). Incidentally, the references A to C in lot numbers show the difference in the manufacturing places (institutions) of the applicant. Measured values were adjusted to three significant figures (Hereinafter, the above is the same for all of measured values).

TABLE 2

| | Content of sulfated tyrosine | |
|---|---|---|
| Lot No. | (ng/unit) | (ng/mL) |
| A01 | 217 | 260 |
| A02 | 344 | 413 |
| A03 | 299 | 359 |
| B01 | 183 | 220 |
| B02 | 198 | 237 |
| B03 | 193 | 232 |
| B04 | 223 | 268 |
| B05 | 205 | 246 |
| B06 | 331 | 397 |
| B07 | 314 | 377 |
| C01 | 179 | 215 |
| C02 | 195 | 234 |
| C03 | 193 | 232 |
| C04 | 188 | 226 |
| C05 | 195 | 234 |
| C06 | 193 | 232 |
| C07 | 257 | 308 |
| C08 | 198 | 237 |
| C09 | 198 | 237 |
| C10 | 184 | 221 |
| C11 | 270 | 324 |
| C12 | 283 | 340 |
| Mean | 218 | 262 |

Example 4 (Measured Result 1 of the Content of Sulfated Tyrosine in the Present Preparation)

The result of measurement of the content of sulfated tyrosine in NTP injection (containing 1.2 units per mL) among the present preparation by the method mentioned in Example 2 is shown in Table 3. The result is shown in terms of the content per unit of the active ingredient of the present preparation ("/unit"), per mL of the present preparation ("/mL") and per ampoule containing 3 mL ("/ampoule").

TABLE 3

| Type of the present preparation | Content of sulfated tyrosine | | |
|---|---|---|---|
| (Identification No.) | (ng/unit) | (ng/mL) | (ng/ampoule) |
| NTP injection (NI01) | 216 | 259 | 777 |
| NTP injection (NI02) | 244 | 293 | 879 |
| NTP injection (NI03) | 228 | 274 | 822 |
| PNT injection (NI04) | 315 | 378 | 1134 |
| NTP injection (NI05) | 297 | 356 | 1070 |
| NTP injection (NI06) | 302 | 362 | 1090 |
| Mean | 267 | 320 | 960 |

Example 5 (Measured Result 2 of the Content of Sulfated Tyrosine in the Present Preparation)

The result of measurement of the content of sulfated tyrosine in NTP tablet (containing 4 units per tablet) among the present preparation by the method mentioned in Example 2 is shown in Table 4. The result is shown in terms of the content per unit of the active ingredient ("/unit") and per tablet ("/tablet").

TABLE 4

| Type of the present preparation | Content of sulfated tyrosine | |
| --- | --- | --- |
| (Identification No.) | (ng/unit) | (ng/tablet) |
| NTP tablet (NT01) | 237 | 948 |
| NTP tablet (NT02) | 161 | 644 |
| NTP tablet (NT03) | 226 | 904 |
| NTP tablet (NT04) | 218 | 872 |
| NTP tablet (NT05) | 230 | 920 |
| NTP tablet (NT06) | 232 | 928 |
| NTP tablet (NT07) | 258 | 1030 |
| NTP tablet (NT08) | 236 | 944 |
| NTP tablet (NT09) | 226 | 904 |
| NTP tablet (NT10) | 242 | 268 |
| NTP tablet (NT11) | 232 | 928 |
| NTP tablet (NT12) | 272 | 1090 |
| NTP tablet (NT13) | 315 | 1260 |
| Mean | 237 | 948 |

Comparative Example 1 (Measured Result of the Content of Sulfated Tyrosine in Other Company's Injections)

The result of measurement of the content of sulfated tyrosine in other company's injections by the same manner as in NTP preparation is shown in Table 5. Incidentally, the distribution of "ROSEMORGEN Inj." has been already finished at the stage of filing the present application and is not available in the market and the following measured result is a result of measurement for the thing which was formerly purchased by the applicant in the market.

TABLE 5

| Type of other company's injections | Content of sulfated tyrosine | |
| --- | --- | --- |
| (Lot No.) | (ng/unit) | (ng/mL) |
| ROSEMORGEN Inj. (2E27B) | 14.9 | 18.0 |
| ROSEMORGEN Inj. (4E57A) | 16.5 | 20.4 |
| NOLPORT Inj. (678405) | 42.6 | 51.6 |
| NOLPORT Inj. (709203) | 35.1 | 42.0 |
| NABUTOPIN Inj. (BD597E) | 41.4 | 49.2 |
| NABUTOPIN Inj. (KF606E) | 35.9 | 43.2 |
| ANALGECINE (20071209) | 108 | 130 |
| ANALGECINE (20080301) | 87 | 104 |

From the above results, it is noted that, even in the same preparation of the extract from inflamed skins of rabbits inoculated with vaccinia virus, the content of sulfated tyrosine is greatly different depending upon the manufacturing company (Tables 3 to 5). It is further noted that, even in the preparation of the same company including the applicant, the content of sulfated tyrosine is sometimes considerably different (Tables 3 to 5). For an extract from inflamed skins of rabbits inoculated with vaccinia virus which is a drug substance for the preparation of the extract from inflamed skins of rabbits inoculated with vaccinia virus, those drug substances of other companies are not available whereby only that which was manufactured by the applicant (NTP extract) was measured. It is noted that, for such a one, there are also scatters to some extent in the content of sulfated tyrosine (Table 2).

However, in the present extract and the present preparation manufactured by the applicant, sulfated tyrosine was contained in an amount of 125 ng/unit or more, more precisely 150 ng/unit or more (Tables 2 to 4). Further, in the present extract and the present preparation manufactured by the applicant, sulfated tyrosine was contained within a range of 125 to 425 ng/unit, more precisely 150 to 400 ng/unit. On the contrary, among the present preparation manufactured by other companies, none of them contained such a high amount of sulfated tyrosine (Table 5). Although it is not clear what is the cause for the difference in the contents of sulfated tyrosine in the present preparation manufactured by each of the companies, it is strongly presumed to be caused by the difference in the manufacturing method for the present preparation in each company. Anyway, as mentioned hereinabove already, the tyrosine sulfation is closely related to the inflammation of the skins of rabbits and a sulfated tyrosine liberated from various kinds of sulfated proteins is able to be utilized as an index for inflammation (inflamed state) of the skin tissues whereby the applicant understands that the fact itself that this substance (component) is contained in more amount in the present preparation (NTP injection) manufactured by the applicant as compared with the injections by other companies constitutes the characteristic and is a favorable characteristic.

As mentioned hereinabove, it is the characteristic of the present extract and the present preparation that 125 ng/unit or more, preferably 150 ng/unit or more of sulfated tyrosine is contained in the present extract and the present preparation. Similarly, it is the characteristic of the present extract and the present preparation that sulfated tyrosine is contained within a range of 125 to 425 ng/unit, preferably 150 to 400 ng/unit.

Further, with regard to the injection containing 1.2 units per mL (hereinafter, it will be referred to as "the present injection") among the present preparation, it constitutes the characteristic of the present injection that 150 ng/mL or more, preferably 180 ng/mL or more of sulfated tyrosine is contained therein. Similarly, it constitutes the characteristic of the present injection that sulfated tyrosine is contained within a range of 150 to 510 ng/mL, preferably 180 to 480 ng/mL. Further, when the present injection is that filled with 3 mL volume in an ampoule (hereinafter, the present injection as such will be referred to as "the present injection of 3 mL ampoule"), it constitutes the characteristic of the present injection of 3 mL ampoule that sulfated tyrosine is contained in an amount of 450 ng/ampoule or more, preferably 540 ng/ampoule or more. Similarly, it constitutes the characteristic of the present injection of 3 mL ampoule that sulfated tyrosine is contained within the range of 450 to 1530 ng/ampoule, preferably 540 to 1440 ng/ampoule.

Further, with regard to the tablet containing 4 units per tablet (hereinafter, it will be referred to as "the present tablet") among the present preparation, it constitutes the characteristic of the present tablet that 500 ng/tablet or more, preferably 600 ng/tablet or more of sulfated tyrosine is contained therein. Similarly, it constitutes the characteristic of the present tablet that sulfated tyrosine is contained within the range of 500 to 1.700 ng/tablet, preferably 600 to 1600 ng/tablet.

In view of the above, it is possible that the content of sulfated tyrosine contained in the present extract and the present preparation is measured so as to confirm whether the present extract and the present preparation are appropriately manufactured whereby the quality thereof is controlled. Thus, it is possible that, when the content of sulfated tyrosine contained in the present extract and the present preparation is measured and, if it is found to be 125 ng/unit or more, preferably 150 ng/unit or more, that is evaluated as being appropriately manufactured. It is further possible to conclude that the present extract and the present preparation are appropriately manufactured by means of such a confirmation that, when the content of sulfated tyrosine contained in the present extract and the present preparation is measured and is found to be within the range of 125 to 425 ng/unit, preferably 150 to 400 ng/unit.

In the case of the present injection, it can be judged that the present injection is appropriately manufactured when the content of sulfated tyrosine contained in the present injection is measured and is found to be 150 ng/mL or more, preferably 180 ng/mL or more. It is further possible to judge that the present injection is appropriately manufactured by measuring the content of sulfated tyrosine contained in the present injection and by confirming to be within the range of 150 to 510 ng/mL, preferably 180 to 480 ng/mL. Similarly, in the case of the present injection of 3 mL ampoule, it is also possible to judge that the 3 mL ampoule injection is appropriately manufactured when the content of sulfated tyrosine contained therein is measured and is found to be 450 ng/ampoule or more, preferably 540 ng/ampoule or more, or when it is within the range of 450 to 1530 ng/ampoule, preferably 540 to 1440 ng/ampoule.

In the case of the present tablet, it can be evaluated that, when the content of sulfated tyrosine contained in the present tablet is measured and is found to be 500 ng/tablet or more, preferably 600 ng/tablet or more, the said tablet is judged to be appropriately manufactured. It is further possible that, when the content of sulfated tyrosine contained in the present tablet is confirmed to be within the range of 500 to 1700 ng/tablet, preferably 600 to 1600 ng/tablet, then the said present tablet is judged to be appropriately manufactured.

In view of the above, the following inventions can be induced as the present invention although those are mere exemplification and the present invention is not limited thereto. Incidentally, in each of the inventions as shown below, the passage reading "by measuring the amount of sulfated tyrosine" is usually used in such a meaning that the amount of sulfated tyrosine is measured for each manufacturing lot of the present extract or the present preparation.

(1) An extract from inflamed skins of rabbits inoculated with vaccinia virus which is judged to be appropriately manufactured by such means that the amount of sulfated tyrosine contained in the extract is measured and the content is confirmed to be 125 ng or more per unit of the extract.

(2) An extract from inflamed skins of rabbits inoculated with vaccinia virus which is judged to be appropriately manufactured by such means that the amount of sulfated tyrosine contained in the extract is measured and the content is confirmed to be 125 to 425 ng per unit of the extract.

(3) An extract being liquid from inflamed skins of rabbits inoculated with vaccinia virus which is judged to be appropriately manufactured by such means that the amount of sulfated tyrosine contained in the extract is measured and the content is confirmed to be 150 ng or more per mL of the extract.

(4) An extract being liquid from inflamed skins of rabbits inoculated with vaccinia virus which is judged to be appropriately manufactured by such means that the amount of sulfated tyrosine contained in the extract is measured and the content is confirmed to be 150 to 510 ng per mL of the extract.

(5) A preparation containing an extract from inflamed skins of rabbits inoculated with vaccinia virus which is judged to be appropriately manufactured by such means that the amount of sulfated tyrosine contained in the preparation is measured and the content is confirmed to be 125 ng or more per unit of the extract in the preparation.

(6) A preparation containing an extract from inflamed skins of rabbits inoculated with vaccinia virus which is judged to be appropriately manufactured by such means that the amount of sulfated tyrosine contained in the preparation is measured and the content is confirmed to be 125 ng to 425 ng per unit of the extract in the preparation.

(7) A preparation containing an extract from inflamed skins of rabbits inoculated with vaccinia virus which is shipped by being judged to be appropriately manufactured by such means that the amount of sulfated tyrosine contained in the preparation is measured and the content is confirmed to be 125 ng or more per unit of the extract in the preparation.

(8) A preparation containing an extract from inflamed skins of rabbits inoculated with vaccinia virus which is shipped by being judged to be appropriately manufactured by such means that the amount of sulfated tyrosine contained in the preparation is measured and the content is confirmed to be 125 to 425 ng per unit of the extract in the preparation.

(9) A preparation containing an extract from inflamed skins of rabbits inoculated with vaccinia virus which is shipped by complying with the standard that the amount of sulfated tyrosine contained in the preparation is measured and the content is found to be 125 ng or more per unit of the extract in the preparation.

(10) A preparation containing an extract from inflamed skins of rabbits inoculated with vaccinia virus which is shipped by complying with the standard that the amount of sulfated tyrosine contained in the preparation is measured and the content is found to be 125 to 425 ng per unit of the extract in the preparation.

(11) An injectable preparation containing an extract from inflamed skins of rabbits inoculated with vaccinia virus which is judged to be appropriately manufactured by such means that the amount of sulfated tyrosine contained in the injectable preparation is measured and the content is confirmed to be 150 ng or more per mL of the injectable preparation.

(12) An injectable preparation containing an extract from inflamed skins of rabbits inoculated with vaccinia virus which is judged to be appropriately manufactured by such means that the amount of sulfated tyrosine contained in the injectable preparation is measured and the content is confirmed to be 150 to 510 ng per mL of the injectable preparation.

(13) An injectable preparation containing an extract from inflamed skins of rabbits inoculated with vaccinia virus which is shipped after being judged to be appropriately manufactured by such means that the amount of sulfated tyrosine contained in the injectable preparation is measured and the content is confirmed to be 1.50 ng or more per mL of the injectable preparation.

(14) An injectable preparation containing an extract from inflamed skins of rabbits inoculated with vaccinia virus which is shipped after being judged to be appropriately manufactured by such means that the amount of sulfated tyrosine contained in the injectable preparation is measured and the content is confirmed to be 150 to 510 ng per mL of the injectable preparation.

(15) An injectable preparation containing an extract from inflamed skins of rabbits inoculated with vaccinia virus which is shipped after complying with the standard that the amount of sulfated tyrosine contained in the injectable preparation is measured and the content is 150 ng or more per mL of the injectable preparation.

(16) An injectable preparation containing an extract from inflamed skins of rabbits inoculated with vaccinia virus which is shipped after complying with the standard that the amount of sulfated tyrosine contained in the injectable preparation is measured and the content is 1.50 to 510 ng per mL of the injectable preparation.

(17) A 3 mL injectable preparation containing an extract from inflamed skins of rabbits inoculated with vaccinia virus which is judged to be appropriately manufactured by such means that the amount of sulfated tyrosine contained in the injectable preparation is measured and the content is confirmed to be 450 ng or more per ampoule of the injectable preparation.

(18) A 3 mL injectable preparation containing an extract from inflamed skins of rabbits inoculated with vaccinia virus which is judged to be appropriately manufactured by such means that the amount of sulfated tyrosine contained in the injectable preparation is measured and the content is confirmed to be 450 to 1530 ng per ampoule of the injectable preparation.

(19) A 3 mL injectable preparation containing an extract from inflamed skins of rabbits inoculated with vaccinia virus which is shipped after being judged to be appropriately manufactured by such means that the amount of sulfated tyrosine contained in the injectable preparation is measured and the content is confirmed to be 450 ng or more per ampoule of the injectable preparation.

(20) A 3 mL injectable preparation containing an extract from inflamed skins of rabbits inoculated with vaccinia virus which is shipped after being judged to be appropriately manufactured by such means that the amount of sulfated tyrosine contained in the injectable preparation is measured and the content is confirmed to be 450 to 1530 ng per ampoule of the injectable preparation.

(21) A 3 mL injectable preparation containing an extract from inflamed skins of rabbits inoculated with vaccinia virus which is shipped after complying with the standard by such means that the amount of sulfated tyrosine contained in the injectable preparation is measured and the content is confirmed to be 450 ng or more per ampoule of the injectable preparation.

(22) A 3 mL injectable preparation containing an extract from inflamed skins of rabbits inoculated with vaccinia virus which is shipped after complying with the standard by such means that the amount of sulfated tyrosine contained in the injectable preparation is measured and the content is confirmed to be 450 to 1530 ng per ampoule of the injectable preparation.

(23) A tablet containing an extract from inflamed skins of rabbits inoculated with vaccinia virus which is judged to be appropriately manufactured by such means that the amount of sulfated tyrosine contained in the tablet is measured and the content is confirmed to be 500 ng or more per tablet.

(24) A tablet containing an extract from inflamed skins of rabbits inoculated with vaccinia virus which is judged to be appropriately manufactured by such means that the amount of sulfated tyrosine contained in the tablet is measured and the content is confirmed to be 500 to 1700 ng per tablet.

(25) A tablet containing an extract from inflamed skins of rabbits inoculated with vaccinia virus which is shipped after being judged to be appropriately manufactured by such means that the amount of sulfated tyrosine contained in the tablet is measured and the content is confirmed to be 500 ng or more per tablet.

(26) A tablet containing an extract from inflamed skins of rabbits inoculated with vaccinia virus which is shipped after being judged to be appropriately manufactured by such means that the amount of sulfated tyrosine contained in the tablet is measured and the content is confirmed to be 500 to 1700 ng per tablet.

(27) A tablet containing an extract from inflamed skins of rabbits inoculated with vaccinia virus which is shipped after complying with the standard that the amount of sulfated tyrosine contained in the tablet is measured and the content is 500 ng or more per tablet.

(28) A tablet containing an extract from inflamed skins of rabbits inoculated with vaccinia virus which is shipped after complying with the standard that the amount of sulfated tyrosine contained in the tablet is measured and the content is 500 to 1700 ng per tablet.

(29) The preparation according to any of (5) to (10), wherein it is an analgesic agent.

(30) The injectable preparation according to any of (11) to (22), wherein it is an analgesic agent.

(31) The tablet according to any of (23) to (28), wherein it is an analgesic agent.

(32) An extract from inflamed skins of rabbits inoculated with vaccinia virus where the amount of sulfated tyrosine contained in the extract is measured and the content is confirmed to be 125 ng or more per unit of the extract.

(33) An extract from inflamed skins of rabbits inoculated with vaccinia virus where the amount of sulfated tyrosine contained in the extract is measured and the content is confirmed to be 125 to 425 ng per unit of the extract.

(34) An extract being liquid from inflamed skins of rabbits inoculated with vaccinia virus where the amount of sulfated tyrosine contained in the extract is measured and the content is confirmed to be 150 ng or more per mL of the extract.

(35) An extract being liquid from inflamed skins of rabbits inoculated with vaccinia virus where the amount of sulfated tyrosine contained in the extract is measured and the content is confirmed to be 150 to 510 ng per mL of the extract.

(36) A preparation containing an extract from inflamed skins of rabbits inoculated with vaccinia virus where the amount of sulfated tyrosine contained in the preparation is measured and the content is confirmed to be 125 ng or more per unit of the extract in the preparation.

(37) A preparation containing an extract from inflamed skins of rabbits inoculated with vaccinia virus where the amount of sulfated tyrosine contained in the preparation is measured and the content is confirmed to be 125 to 425 ng per unit of the extract in the preparation.

(38) An injectable preparation containing an extract from inflamed skins of rabbits inoculated with vaccinia virus where the amount of sulfated tyrosine contained in the injectable preparation is measured and the content is confirmed to be 150 ng or more per mL of the injectable preparation.

(39) An injectable preparation containing an extract from inflamed skins of rabbits inoculated with vaccinia virus where the amount of sulfated tyrosine contained in the injectable preparation is measured and the content is confirmed to be 150 to 510 ng per mL of the injectable preparation.

(40) A 3 mL injectable preparation containing an extract from inflamed skins of rabbits inoculated with vaccinia virus where the amount of sulfated tyrosine contained in the injectable preparation is measured and the content is confirmed to be 450 ng or more per ampoule of the injectable preparation.

(41) A 3 mL injectable preparation containing an extract from inflamed skins of rabbits inoculated with vaccinia virus where the amount of sulfated tyrosine contained in the injectable preparation is measured and the content is confirmed to be 450 to 1530 ng per ampoule of the injectable preparation.

(42) A tablet containing an extract from inflamed skins of rabbits inoculated with vaccinia virus where the amount of sulfated tyrosine contained in the tablet is measured and the content is confirmed to be 500 ng or more per tablet.

(43) A tablet containing an extract from inflamed skins of rabbits inoculated with vaccinia virus where the amount of sulfated tyrosine contained in the tablet is measured and the content is confirmed to be 500 to 1700 ng per tablet.

(44) The preparation according to (36) or (37), wherein it is an analgesic agent.

(45) The injectable preparation according to any of (38) to (41), wherein it is an analgesic agent.

(46) The tablet according to (42) or (43), wherein it is an analgesic agent.

(47) A preparation containing an extract from inflamed skins of rabbits inoculated with vaccinia virus, wherein the amount of sulfated tyrosine contained in the preparation before shipping is measured and the content is confirmed to be 125 ng or more per unit of the extract in the preparation.

(48) A preparation containing an extract from inflamed skins of rabbits inoculated with vaccinia virus, wherein the amount of sulfated tyrosine contained in the preparation before shipping is measured and the content is confirmed to be 125 to 425 ng per unit of the extract in the preparation.

(49) An injectable preparation containing an extract from inflamed skins of rabbits inoculated with vaccinia virus, wherein the amount of sulfated tyrosine contained in the injectable preparation before shipping is measured and the content is confirmed to be 150 ng or more per mL of the injectable preparation.

(50) An injectable preparation containing an extract from inflamed skins of rabbits inoculated with vaccinia virus, wherein the amount of sulfated tyrosine contained in the injectable preparation before shipping is measured and the content is confirmed to be 150 to 510 ng per mL of the injectable preparation.

(51) A 3 mL, injectable preparation containing an extract from inflamed skins of rabbits inoculated with vaccinia virus, wherein the amount of sulfated tyrosine contained in the injectable preparation before shipping is measured and the content is confirmed to be 450 ng or more per ampoule of the injectable preparation.

(52) A 3 mL injectable preparation containing an extract from inflamed skins of rabbits inoculated with vaccinia virus, wherein the amount of sulfated tyrosine contained in the injectable preparation before shipping is measured and the content is confirmed to be 450 to 1530 ng per ampoule of the injectable preparation.

(53) A tablet containing an extract from inflamed skins of rabbits inoculated with vaccinia virus, wherein the amount of sulfated tyrosine contained in the tablet before shipping is measured and the content is confirmed to be 500 ng or more per tablet.

(54) A tablet containing an extract from inflamed skins of rabbits inoculated with vaccinia virus, wherein the amount of sulfated tyrosine contained in the tablet before shipping is measured and the content is confirmed to be 500 to 1700 ng per tablet.

(55) The preparation according to (47) or (48), wherein it is an analgesic agent.

(56) The injectable preparation according to any of (49) to (52), wherein it is an analgesic agent.

(57) The tablet according to (53) or (54), wherein it is an analgesic agent.

(58) A method for inspection where the amount of sulfated tyrosine contained in an extract from inflamed skins of rabbits inoculated with vaccinia virus is measured and, when the content is 125 ng or more per unit of the extract, the manufacture of the extract is judged to be appropriately conducted.

(59) A method for inspection where the amount of sulfated tyrosine contained in an extract from inflamed skins of rabbits inoculated with vaccinia virus is measured and, when the content is 125 to 425 ng per unit of the extract, the manufacture of the extract is judged to be appropriately conducted.

(60) A method for inspection where the amount of sulfated tyrosine contained in a preparation which contains an extract from inflamed skins of rabbits inoculated with vaccinia virus is measured and, when the content is 125 ng or more per unit of the extract in the preparation, the manufacture of the preparation is judged to be appropriately conducted.

(61) A method for inspection where the amount of sulfated tyrosine contained in a preparation which contains an extract from inflamed skins of rabbits inoculated with vaccinia virus is measured and, when the content is 125 to 425 ng per unit of the extract in the preparation, the manufacture of the preparation is judged to be appropriately conducted.

(62) A method for inspection where the amount of sulfated tyrosine contained in an injectable preparation which contains an extract from inflamed skins of rabbits inoculated with vaccinia virus is measured and, when the content is 150 ng or more per mL of the injectable preparation, the manufacture of the injectable preparation is judged to be appropriately conducted.

(63) A method for inspection where the amount of sulfated tyrosine contained in an injectable preparation which contains an extract from inflamed skins of rabbits inoculated with vaccinia virus is measured and, when the content is 150 to 510 ng per mL of the injectable preparation, the manufacture of the injectable preparation is judged to be appropriately conducted.

(64) A method for inspection where the amount of sulfated tyrosine contained in a 3 mL injectable preparation which contains an extract from inflamed skins of rabbits inoculated with vaccinia virus is measured and, when the content is 450 ng or more per ampoule of the injectable preparation, the manufacture of the injectable preparation is judged to be appropriately conducted.

(65) A method for inspection where the amount of sulfated tyrosine contained in a 3 mL injectable preparation which contains an extract from inflamed skins of rabbits inoculated with vaccinia virus is measured and, when the content is 450 to 1530 ng per ampoule of the injectable preparation, the manufacture of the injectable preparation is judged to be appropriately conducted.

(66) A method for inspection where the amount of sulfated tyrosine contained in a tablet which contains an extract from inflamed skins of rabbits inoculated with vaccinia virus is measured and, when the content is 500 ng or more per tablet, the manufacture of the tablet is judged to be appropriately conducted.

(67) A method for inspection where the amount of sulfated tyrosine contained in a tablet which contains an extract from inflamed skins of rabbits inoculated with vaccinia virus is measured and, when the content is 500 to 1700 ng per tablet, the manufacture of the tablet is judged to be appropriately conducted.

(68) A method for controlling the manufacture of an extract from inflamed skins of rabbits inoculated with vaccinia virus where, when the amount of sulfated tyrosine contained in the extract is 125 ng or more per unit of the extract, the manufacture of the extract is judged to be appropriately conducted.

(69) A method for controlling the manufacture of an extract from inflamed skins of rabbits inoculated with vaccinia virus where, when the amount of sulfated tyrosine contained in the extract is 125 to 425 ng per unit of the extract, the manufacture of the extract is judged to be appropriately conducted.

(70) A method for controlling the manufacture of a preparation containing an extract from inflamed skins of rabbits inoculated with vaccinia virus where, when the amount of sulfated tyrosine contained in the preparation is 125 ng or more per unit of the extract in the preparation, the manufacture of the preparation is judged to be appropriately conducted.

(71) A method for controlling the manufacture of a preparation containing an extract from inflamed skins of rabbits inoculated with vaccinia virus where, when the amount of sulfated tyrosine contained in the preparation is 125 to 425 ng per unit of the extract in the preparation, the manufacture of the preparation is judged to be appropriately conducted.

(72) A method for controlling the manufacture of an injectable preparation containing an extract from inflamed skins of rabbits inoculated with vaccinia virus where, when the amount of sulfated tyrosine contained in the injectable preparation is 150 ng or more per mL of the injectable preparation, the manufacture of the injectable preparation is judged to be appropriately conducted.

(73) A method for controlling the manufacture of an injectable preparation containing an extract from inflamed skins of rabbits inoculated with vaccinia virus where, when the amount of sulfated tyrosine contained in the injectable preparation is 150 to 510 ng per mL of the injectable preparation, the manufacture of the injectable preparation is judged to be appropriately conducted.

(74) A method for controlling the manufacture of a 3 mL injectable preparation containing an extract from inflamed skins of rabbits inoculated with vaccinia virus where, when the amount of sulfated tyrosine contained in the injectable preparation is 450 ng or more per ampoule of the injectable preparation, the manufacture of the injectable preparation is judged to be appropriately conducted.

(75) A method for controlling the manufacture of a 3 mL injectable preparation containing an extract from inflamed skins of rabbits inoculated with vaccinia virus where, when the amount of sulfated tyrosine contained in the injectable preparation is 450 to 1530 ng per ampoule of the injectable preparation, the manufacture of the injectable preparation is judged to be appropriately conducted.

(76) A method for controlling the manufacture of a tablet containing an extract from inflamed skins of rabbits inoculated with vaccinia virus where, when the amount of sulfated tyrosine contained in the tablet is 500 ng or more per tablet, the manufacture of the tablet is judged to be appropriately conducted.

(77) A method for controlling the manufacture of a tablet containing an extract from inflamed skins of rabbits inoculated with vaccinia virus where, when the amount of sulfated tyrosine contained in the tablet is 500 to 1700 ng per tablet, the manufacture of the tablet is judged to be appropriately conducted.

(78) Use of an extract from inflamed skins of rabbits inoculated with vaccinia virus where the content of sulfated tyrosine in the manufacture of a preparation containing the extract is 125 ng or more per unit of the extract.

(79) Use of an extract from inflamed skins of rabbits inoculated with vaccinia virus where the content of sulfated tyrosine in the manufacture of a preparation containing the extract is 125 to 425 ng per unit of the extract.

(80) Use of an extract from inflamed skins of rabbits inoculated with vaccinia virus where the content of sulfated tyrosine in the manufacture of a preparation containing the extract is 150 ng or more per mL of the extract.

(81) Use of an extract from inflamed skins of rabbits inoculated with vaccinia virus where the content of sulfated tyrosine in the manufacture of a preparation containing the extract is 150 to 510 ng per mL of the extract.

(82) A method for shipping a preparation containing an extract from inflamed skins of rabbits inoculated with vaccinia virus where the amount of sulfated tyrosine contained in the preparation is measured and, when the content is confirmed to be 125 ng or more per unit of the extract, the preparation is judged to be appropriately manufactured and is judged to be able to be shipped.

(83) A method for shipping a preparation containing an extract from inflamed skins of rabbits inoculated with vaccinia virus where the amount of sulfated tyrosine contained in the preparation is measured and, when the content is confirmed to be 125 to 425 ng per unit of the extract, the preparation is judged to be appropriately manufactured and is judged to be able to be shipped.

(84) A method for shipping an injectable preparation containing an extract from inflamed skins of rabbits inoculated with vaccinia virus where the amount of sulfated tyrosine contained in the injectable preparation is measured and, when the content is confirmed to be 150 ng or more per mL of the injectable preparation, the injectable preparation is judged to be appropriately manufactured and is judged to be able to be shipped.

(85) A method for shipping an injectable preparation containing an extract from inflamed skins of rabbits inoculated with vaccinia virus where the amount of sulfated tyrosine contained in the injectable preparation is measured and, when the content is confirmed to be 150 to 510 ng per mL of the injectable preparation, the injectable preparation is judged to be appropriately manufactured and is judged to be able to be shipped.

(86) A method for shipping a 3 mL injectable preparation containing an extract from inflamed skins of rabbits inoculated with vaccinia virus where the amount of sulfated tyrosine contained in the injectable preparation is measured and, when the content is confirmed to be 450 ng or more per ampoule of the injectable preparation, the injectable preparation is judged to be appropriately manufactured and is judged to be able to be shipped.

(87) A method for shipping a 3 mL injectable preparation containing an extract from inflamed skins of rabbits inoculated with vaccinia virus where the amount of sulfated tyrosine contained in the injectable preparation is measured and, when the content is confirmed to be 450 to 1530 ng per ampoule of the injectable preparation, the injectable preparation is judged to be appropriately manufactured and is judged to be able to be shipped.

(88) A method for shipping a tablet containing an extract from inflamed skins of rabbits inoculated with vaccinia virus where the amount of sulfated tyrosine contained in the tablet is measured and, when the content is confirmed to be 500 ng or more per tablet, the tablet is judged to be appropriately manufactured and is judged to be able to be shipped.

(89) A method for shipping a tablet containing an extract from inflamed skins of rabbits inoculated with vaccinia virus where the amount of sulfated tyrosine contained in the tablet is measured and, when the content is confirmed to be 500 to 1700 ng per tablet, the tablet is judged to be appropriately manufactured and is judged to be able to be shipped.

(90) A preparation containing an extract from inflamed skins of rabbits inoculated with vaccinia virus which is shipped by the shipping method according to (82) or (83).

(91) An injectable preparation containing an extract from inflamed skins of rabbits inoculated with vaccinia virus which is shipped by the shipping method according to any of (84) to (87).

(92) A tablet containing an extract from inflamed skins of rabbits inoculated with vaccinia virus which is shipped by the shipping method according to (88) or (89).

(93) A preparation containing an extract from inflamed skins of rabbits inoculated with vaccinia virus, wherein the variations in the effect of the preparation among the manufacturing lots are reduced by such a means that the amount of sulfated tyrosine contained in the preparation is measured for each manufacturing lot and the content is confirmed to be 125 ng or more per unit of the extract in the preparation.

(94) A preparation containing an extract from inflamed skins of rabbits inoculated with vaccinia virus, wherein the variations in the effect of the preparation among the manufacturing lots are reduced by such a means that the amount of sulfated tyrosine contained in the preparation is measured for each manufacturing lot and the content is confirmed to be 125 to 425 ng per unit of the extract in the preparation.

(95) An injectable preparation containing an extract from inflamed skins of rabbits inoculated with vaccinia virus, wherein the variations in the effect of the injectable preparation among the manufacturing lots are reduced by such a means that the amount of sulfated tyrosine contained in the injectable preparation is measured for each manufacturing lot and the content is confirmed to be 150 ng or more per mL of the injectable preparation.

(96) An injectable preparation containing an extract from inflamed skins of rabbits inoculated with vaccinia virus, wherein the variations in the effect of the injectable preparation among the manufacturing lots are reduced by such a means that the amount of sulfated tyrosine contained in the injectable preparation is measured for each manufacturing lot and the content is confirmed to be 150 to 510 ng per mL of the injectable preparation.

(97) A 3 mL injectable preparation containing an extract from inflamed skins of rabbits inoculated with vaccinia virus, wherein the variations in the effect of the injectable preparation among the manufacturing lots are reduced by such a means that the amount of sulfated tyrosine contained in the injectable preparation is measured for each manufacturing lot and the content is confirmed to be 450 ng or more per ampoule of the injectable preparation.

(98) A 3 mL injectable preparation containing an extract from inflamed skins of rabbits inoculated with vaccinia virus, wherein the variations in the effect of the injectable preparation among the manufacturing lots are reduced by such a means that the amount of sulfated tyrosine contained in the injectable preparation is measured for each manufacturing lot and the content is confirmed to be 450 to 1530 ng per ampoule of the injectable preparation.

(99) A tablet containing an extract from inflamed skins of rabbits inoculated with vaccinia virus, wherein the variations in the effect of the tablet among the manufacturing lots are reduced by such a means that the amount of sulfated tyrosine contained in the tablet is measured for each manufacturing lot and the content is confirmed to be 500 ng or more per tablet.

(100) A tablet containing an extract from inflamed skins of rabbits inoculated with vaccinia virus, wherein the variations in the effect of the tablet among the manufacturing lots are reduced by such a means that the amount of sulfated tyrosine contained in the tablet is measured for each manufacturing lot and the content is confirmed to be 500 to 1700 ng per tablet.

(101) The preparation according to (93) or (94), wherein the effect is an analgesic effect.

(102) The preparation according to (93) or (94), wherein the variations among the manufacturing lots are due to the difference in the inflamed state of skin tissues of rabbits inoculated with vaccinia virus.

(103) The injectable preparation according to any of (95) to (98), wherein the effect is an analgesic effect.

(104) The injectable preparation according to any of (95) to (98), wherein the variations among the manufacturing lots are due to the difference in the inflamed state of skin tissues of rabbits inoculated with vaccinia virus.

(105) The tablet according to (99) or (100), wherein the effect is an analgesic effect.

(106) The tablet according to (99) or (100), wherein the variations among the manufacturing lots are due to the difference in the inflamed state of skin tissues of rabbits inoculated with vaccinia virus.

(107) A method for controlling the manufacture of a preparation containing an extract from inflamed skins of rabbits inoculated with vaccinia virus in which the variations in the effect of the preparation among manufacturing lots are reduced, wherein the manufacture of the preparation is judged to be appropriately conducted in such a case that the amount of sulfated tyrosine contained in the preparation is measured for each manufacturing lot and that the content is 125 ng or more per unit of the extract in the preparation.

(108) A method for controlling the manufacture of a preparation containing an extract from inflamed skins of rabbits inoculated with vaccinia virus in which the variations in the effect of the preparation among manufacturing lots are reduced, wherein the manufacture of the preparation is judged to be appropriately conducted in such a case that the amount of sulfated tyrosine contained in the preparation is measured for each manufacturing lot and that the content is 125 to 425 ng per unit of the extract in the preparation.

(109) A method for controlling the manufacture of an injectable preparation containing an extract from inflamed skins of rabbits inoculated with vaccinia virus in which the variations in the effect of the injectable preparation among manufacturing lots are reduced, wherein the manufacture of the injectable preparation is judged to be appropriately conducted in such a case that the amount of sulfated tyrosine contained in the injectable preparation is measured for each manufacturing lot and that the content is 150 ng or more per mL, of the injectable preparation.

(110) A method for controlling the manufacture of an injectable preparation containing an extract from inflamed skins of rabbits inoculated with vaccinia virus in which the variations in the effect of the injectable preparation among manufacturing lots are reduced, wherein the manufacture of the injectable preparation is judged to be appropriately conducted in such a case that the amount of sulfated tyrosine contained in the injectable preparation is measured for each manufacturing lot and that the content is 150 to 510 ng per mL of the injectable preparation.

(111) A method for controlling the manufacture of a 3 mL injectable preparation containing an extract from inflamed skins of rabbits inoculated with vaccinia virus in which the variations in the effect of the injectable preparation among manufacturing lots are reduced, wherein the manufacture of the injectable preparation is judged to be appropriately conducted in such a case that the amount of sulfated tyrosine contained in the injectable preparation is measured for each manufacturing lot and that the content is 450 ng or more per ampoule of the injectable preparation.

(112) A method for controlling the manufacture of a 3 mL injectable preparation containing an extract from inflamed skins of rabbits inoculated with vaccinia virus in which the variations in the effect of the injectable preparation among manufacturing lots are reduced, wherein the manufacture of the injectable preparation is judged to be appropriately conducted in such a case that the amount of sulfated tyrosine contained in the injectable preparation is measured for each manufacturing lot and that the content is 450 to 1530 ng per ampoule of the injectable preparation.

(113) A method for controlling the manufacture of a tablet containing an extract from inflamed skins of rabbits inoculated with vaccinia virus in which the variations in the effect of the tablet among manufacturing lots are reduced, wherein the manufacture of the tablet is judged to be appropriately conducted in such a case that the amount of sulfated tyrosine contained in the tablet is measured for each manufacturing lot and that the content is 500 ng or more per tablet.

(114) A method for controlling the manufacture of a tablet containing an extract from inflamed skins of rabbits inoculated with vaccinia virus in which the variations in the effect of the tablet among manufacturing lots are reduced, wherein manufacture of the tablet is judged to be appropriately conducted in such a case that the amount of sulfated tyrosine contained in the tablet is measured for each manufacturing lot and that the content is 500 to 1700 ng per tablet.

(115) The method for controlling the manufacture according to any of (107) to (114), wherein the effect is an analgesic effect.

(116) The method for controlling the manufacture according to any of (107) to (114), wherein the variations among the manufacturing lots are due to the difference in the inflamed state of skin tissues of rabbits inoculated with vaccinia virus.

(117) A preparation containing an extract from inflamed skins of rabbits inoculated with vaccinia virus, wherein the manufacture is controlled by the method according to (107) or (108).

(118) An injectable preparation containing an extract from inflamed skins of rabbits inoculated with vaccinia virus, wherein the manufacture is controlled by the method according to any of (109) to (112).

(119) A tablet containing an extract from inflamed skins of rabbits inoculated with vaccinia virus, wherein the manufacture by the method according to (113) or (114).

(120) A preparation, an injectable preparation or a tablet, wherein the manufacture is controlled by the method according to (115).

(121) A preparation, an injectable preparation or a tablet, wherein the manufacture is controlled by the method according to (116).

(122) A method for inspection of a preparation containing an extract from inflamed skins of rabbits inoculated with vaccinia virus in which the variations of the effect of the preparation are reduced, wherein the manufacture of the preparation is judged to be appropriately conducted in such a case that the amount of sulfated tyrosine contained in the preparation is measured for each manufacturing lot and that the content is 125 ng or more per unit of the extract in the preparation.

(123) A method for inspection of a preparation containing an extract from inflamed skins of rabbits inoculated with vaccinia virus in which the variations of the effect of the preparation are reduced, wherein the manufacture of the preparation is judged to be appropriately conducted in such a case that the amount of sulfated tyrosine contained in the preparation is measured for each manufacturing lot and that the content is 125 to 425 ng per unit of the extract in the preparation.

(124) A method for inspection of an injectable preparation containing an extract from inflamed skins of rabbits inoculated with vaccinia virus in which the variations of the effect of the injectable preparation are reduced, wherein the manufacture of the injectable preparation is judged to be appropriately conducted in such a case that the amount of sulfated tyrosine contained in the injectable preparation is measured for each manufacturing lot and that the content is 150 ng or more per mL of the injectable preparation.

(125) A method for inspection of an injectable preparation containing an extract from inflamed skins of rabbits inoculated with vaccinia virus in which the variations of the effect of the injectable preparation are reduced, wherein the manufacture of the injectable preparation is judged to be appropriately conducted in such a case that the amount of sulfated tyrosine contained in the injectable preparation is measured for each manufacturing lot and that the content is 150 to 510 ng per mL of the injectable preparation.

(126) A method for inspection of a 3 mL injectable preparation containing an extract from inflamed skins of rabbits inoculated with vaccinia virus in which the variations of the effect of the injectable preparation are reduced, wherein the manufacture of the injectable preparation is judged to be appropriately conducted in such a case that the amount of sulfated tyrosine contained in the injectable preparation is measured for each manufacturing lot and that the content is 450 ng or more per ampoule of the injectable preparation.

(127) A method for inspection of a 3 mL injectable preparation containing an extract from inflamed skins of rabbits inoculated with vaccinia virus in which the variations of the effect of the injectable preparation are reduced, wherein the manufacture of the injectable preparation is judged to be appropriately conducted in such a case that the amount of sulfated tyrosine contained in the injectable preparation is measured for each manufacturing lot and that the content is 450 to 1530 ng per ampoule of the injectable preparation.

(128) A method for inspection of a tablet containing an extract from inflamed skins of rabbits inoculated with vaccinia virus in which the variations of the effect of the tablet are reduced, wherein the manufacture of the tablet is judged to be appropriately conducted in such a case that the amount of sulfated tyrosine contained in the tablet is measured for each manufacturing lot and that the content is 500 ng or more per tablet.

(129) A method for inspection of a tablet containing an extract from inflamed skins of rabbits inoculated with vaccinia virus in which the variations of the effect of the tablet are reduced, wherein the manufacture of the tablet is judged to be appropriately conducted in such a case that the amount of sulfated tyrosine contained in the tablet is measured for each manufacturing lot and that the content is 500 to 1700 ng per tablet.

(130) The method for inspection according to any of (122) to (129), wherein the effect is an analgesic effect.

(131) The method for inspection according to any of (122) to (129), wherein the variations among the manufacturing lots are due to the difference in the inflamed state of skin tissues of rabbits inoculated with vaccinia virus.

(132) A preparation containing an extract from inflamed skins of rabbits inoculated with vaccinia virus inspected by the method of inspection according to (122) or (123).

(133) An injectable preparation containing an extract from inflamed skins of rabbits inoculated with vaccinia virus inspected by the method of inspection according to any of (124) to (127).

(134) A tablet containing an extract from inflamed skins of rabbits inoculated with vaccinia virus inspected by the method of inspection according to (128) or (129).

(135) A preparation, an injectable preparation or a tablet inspected by the method for inspection according to (130).

(136) A preparation, an injectable preparation or a tablet inspected by the method for inspection according to (131).

(137) A method for shipping a preparation containing an extract from inflamed skins of rabbits inoculated with vaccinia virus in which the variations of the effect of the preparation among the manufacturing lots are reduced, wherein the amount of sulfated tyrosine contained in the preparation is measured for each manufacturing lot and, in case the content is confirmed to be 125 ng or more per unit of the extract, the preparation is judged to be appropriately manufactured.

(138) A method for shipping a preparation containing an extract from inflamed skins of rabbits inoculated with vaccinia virus in which the variations of the effect of the preparation among the manufacturing lots are reduced, wherein the amount of sulfated tyrosine contained in the preparation is measured for each manufacturing lot and, in case the content is confirmed to be 125 to 425 ng per unit of the extract, the preparation is judged to be appropriately manufactured.

(139) A method for shipping an injectable preparation containing an extract from inflamed skins of rabbits inoculated with vaccinia virus in which the variations of the effect of the injectable preparation among the manufacturing lots are reduced, wherein the amount of sulfated tyrosine contained in the injectable preparation is measured for each manufacturing lot and, in case the content is confirmed to be 150 ng or more per mL of the injectable preparation, the injectable preparation is judged to be appropriately manufactured.

(140) A method for shipping an injectable preparation containing an extract from inflamed skins of rabbits inoculated with vaccinia virus in which the variations of the effect of the injectable preparation among the manufacturing lots are reduced, wherein the amount of sulfated tyrosine contained in the injectable preparation is measured for each manufacturing lot and, in case the content is confirmed to be 150 to 510 ng per mL of the injectable preparation, the injectable preparation is judged to be appropriately manufactured.

(141) A method for shipping a 3 mL injectable preparation containing an extract from inflamed skins of rabbits inoculated with vaccinia virus in which the variations of the effect of the injectable preparation among the manufacturing lots are reduced, wherein the amount of sulfated tyrosine contained in the injectable preparation is measured for each manufacturing lot and, in case the content is confirmed to be 450 ng or more per ampoule of the injectable preparation, the injectable preparation is judged to be appropriately manufactured.

(142) A method for shipping a 3 mL injectable preparation containing an extract from inflamed skins of rabbits inoculated with vaccinia virus in which the variations of the effect of the injectable preparation among the manufacturing lots are reduced, wherein the amount of sulfated tyrosine contained in the injectable preparation is measured for each manufacturing lot and, in case the content is confirmed to be 450 to 1530 ng per ampoule of the injectable preparation, the injectable preparation is judged to be appropriately manufactured.

(143) A method for shipping a tablet containing an extract from inflamed skins of rabbits inoculated with vaccinia virus in which the variations of the effect of the tablet among the manufacturing lots are reduced, wherein the amount of sulfated tyrosine contained in the tablet is measured for each manufacturing lot and, in case the content is confirmed to be 500 ng or more per tablet, the tablet is judged to be appropriately manufactured.

(144) A method for shipping a tablet containing an extract from inflamed skins of rabbits inoculated with vaccinia virus in which the variations of the effect of the tablet among the manufacturing lots are reduced, wherein the amount of sulfated tyrosine contained in the tablet is measured for each manufacturing lot and, in case the content is confirmed to be 500 to 1700 ng per tablet, the tablet is judged to be appropriately manufactured.

(145) The method for shipping according to any of (137) to (144), wherein the effect is an analgesic effect.

(146) The method for shipping according to any of (137) to (144), wherein the variations among the manufacturing lots are due to the difference in the inflamed state of skin tissues of rabbits inoculated with vaccinia virus.

(147) A preparation containing an extract from inflamed skins of rabbits inoculated with vaccinia virus shipped by the method for shipping according to (137) or (138).

(148) An injectable preparation containing an extract from inflamed skins of rabbits inoculated with vaccinia virus shipped by the method for shipping according to any of (139) to (142).

(149) A tablet containing an extract from inflamed skins of rabbits inoculated with vaccinia virus shipped by the method for shipping according to (143) or (144).

(150) A preparation, an injectable preparation or a tablet shipped by the method for shipping according to (145).

(151) A preparation, an injectable preparation or a tablet shipped by the method for shipping according to (146).

(152) A method for manufacturing an extract from inflamed skins of rabbits inoculated with vaccinia virus which is characterized in that an extraction solvent is added to crushed inflamed tissues and allowed to stand for 5 to 12 days.

(153) The method for manufacturing an extract from inflamed skins of rabbits inoculated with vaccinia virus according to (152), wherein warming at 30 to 45° C. with or without stirring is conducted during the period where an extraction solvent is added to crushed inflamed tissues and allowed to stand for 5 to 12 days.

(154) The method for manufacturing an extract from inflamed skins of rabbits inoculated with vaccinia virus according to (153), wherein after an extraction solvent is added to a crushed inflamed tissues and allowed to stand for 3 to 7 days, it is warmed at 35 to 40° C. with stirring for 3 to 4 days more.

(155) The method for manufacturing an extract from inflamed skins of rabbits inoculated with vaccinia virus according to any of (152) to (154), wherein the extraction solvent to be added to the crushed inflamed tissues is a phenol solution.

(156) The method for manufacturing an extract from inflamed skins of rabbits inoculated with vaccinia virus according to (155), wherein the amount of the phenol solution is one- to five-fold of the amount of the crushed inflamed tissues.

(157) An extract from inflamed skins of rabbits inoculated with vaccinia virus which is manufactured by the manufacturing method according to any of (152) to (156).

(158) The extract from inflamed skins of rabbits inoculated with vaccinia virus according to (157), wherein the amount of sulfated tyrosine contained in the extract is 125 ng or more per unit of the extract.

(159) The extract from inflamed skins of rabbits inoculated with vaccinia virus according to (157), wherein the amount of sulfated tyrosine contained in the extract is 125 to 425 ng per unit of the extract.

(160) A preparation containing the extract from inflamed skins of rabbits inoculated with vaccinia virus manufactured by the manufacturing method according to any of (152) to (156).

(161) The preparation according to (160), wherein the preparation is an injectable preparation.

(162) The preparation according to (160), wherein the preparation is a 3 mL injectable preparation.

(163) The preparation according to (160), wherein the preparation is a tablet.

(164) The preparation according to (160), wherein the amount of sulfated tyrosine contained in the preparation is 125 ng or more per unit of the extract from inflamed skins of rabbits inoculated with vaccinia virus contained in the preparation.

(165) The preparation according to (160), wherein the amount of sulfated tyrosine contained in the preparation is 125 to 425 ng per unit of the extract from inflamed skins of rabbits inoculated with vaccinia virus contained in the preparation.

(166) The preparation according to (161), wherein the amount of sulfated tyrosine contained in the injectable preparation is 150 ng or more per mL of the injectable preparation.

(167) The preparation according to (161), wherein the amount of sulfated tyrosine contained in the injectable preparation is 150 to 510 ng per mL of the injectable preparation.

(168) The preparation according to (162), wherein the amount of sulfated tyrosine contained in the injectable preparation is 450 ng or more per ampoule of the injectable preparation.

(169) The preparation according to (162), wherein the amount of sulfated tyrosine contained in the injectable preparation is 450 to 1530 ng per ampoule of the injectable preparation.

(170) The preparation according to (163), wherein the amount of sulfated tyrosine contained in the tablet is 500 ng or more per tablet.

(171) The preparation according to (163), wherein the amount of sulfated tyrosine contained in the tablet is 500 to 1.700 ng per tablet.

(172) An extract from inflamed skins of rabbits inoculated with vaccinia virus, which is characterized in that, the variations in the content of sulfated tyrosine among the manufacturing lots are reduced so that the amount of sulfated tyrosine contained in the extract is made 125 ng or more per unit of the extract by such a means that, during the steps for the manufacture of the extract, there is conducted a step where an extraction solvent is added to crushed inflamed tissues, allowed to stand for 3 to 7 days and warmed at 30 to 45° C. for 3 to 4 days more.

(173) The extract from inflamed skins of rabbits inoculated with vaccinia virus according to (172), wherein the content of sulfated tyrosine is 125 to 425 ng per unit of the extract.

(174) The extract from inflamed skins of rabbits inoculated with vaccinia virus according to (172) or (173), wherein the warming step for 3 to 4 days in the steps of manufacturing the extract from inflamed skins of rabbits inoculated with vaccinia virus is a step of warming at 35 to 40° C. with stirring.

(175) An extract being liquid from inflamed skins of rabbits inoculated with vaccinia virus, which is characterized in that, the variations in the content of sulfated tyrosine among the manufacturing lots are reduced so that the amount of sulfated tyrosine contained in the extract is made 150 ng or more per mL of the extract by such a means that, during the steps for the manufacture of the extract, there is conducted a step where an extraction solvent is added to crushed inflamed tissues, allowed to stand for 3 to 7 days and warmed at 30 to 45° C. for 3 to 4 days more.

(176) The extract being liquid from inflamed skins of rabbits inoculated with vaccinia virus according to (175), wherein the content of sulfated tyrosine is 150 to 510 ng per mL of the extract.

(177) The extract being liquid from inflamed skins of rabbits inoculated with vaccinia virus according to (175) or (176), wherein the warming step for 3 to 4 days in the steps of manufacturing the extract from inflamed skins of rabbits inoculated with vaccinia virus is a step of warming at 35 to 40° C. with stirring.

(178) A preparation containing the extract from inflamed skins of rabbits inoculated with vaccinia virus according to (172) or (174), which is characterized in that the variations in the content of sulfated tyrosine among the manufacturing lots are reduced so that the amount of sulfated tyrosine contained in the preparation is made 125 ng or more per unit of the extract in the preparation.

(179) A preparation containing the extract from inflamed skins of rabbits inoculated with vaccinia virus according to (173) or (174), which is characterized in that, the variations in the content of sulfated tyrosine among the manufacturing lots are reduced so that the amount of sulfated tyrosine contained in the preparation is made 125 to 425 ng per unit of the extract in the preparation.

(180) An injectable preparation containing the extract from inflamed skins of rabbits inoculated with vaccinia virus according to (175) or (177), which is characterized in that the variations in the content of sulfated tyrosine among the manufacturing lots are reduced so that the amount of sulfated tyrosine contained in the injectable preparation is made 150 ng or more per mL of the injectable preparation.

(181) An injectable preparation containing the extract from inflamed skins of rabbits inoculated with vaccinia virus according to (176) or (177), which is characterized in that the variations in the content of sulfated tyrosine among the manufacturing lots are reduced so that the amount of sulfated tyrosine contained in the injectable preparation is made 150 to 510 ng per mL of the injectable preparation.

(182) A 3 mL injectable preparation containing the extract from inflamed skins of rabbits inoculated with vaccinia virus according to (175) or (177), which is characterized in that the variations in the content of sulfated tyrosine among the manufacturing lots are reduced so that the amount of sulfated tyrosine contained in the injectable preparation is made 450 ng or more per ampoule of the injectable preparation.

(183) A 3 mL injectable preparation containing the extract from inflamed skins of rabbits inoculated with vaccinia virus according to (176) or (177), which is characterized in that the variations in the content of sulfated tyrosine among the manufacturing lots are reduced so that the amount of sulfated tyrosine contained in the injectable preparation is made 450 to 1530 ng per ampoule of the injectable preparation.

(184) A tablet containing the extract from inflamed skins of rabbits inoculated with vaccinia virus according to (175) or (177), which is characterized in that the variations in the content of sulfated tyrosine among the manufacturing lots are reduced so that the amount of sulfated tyrosine contained in the tablet is made 500 ng or more per tablet.

(185) A tablet containing the extract from inflamed skins of rabbits inoculated with vaccinia virus according to (176) or (177), which is characterized in that the variations in the content of sulfated tyrosine among the manufacturing lots are reduced so that the amount of sulfated tyrosine contained in the tablet is made 500 to 1700 ng per tablet.

(186) The preparation according to (178) or (179), wherein it is an analgesic agent.

(187) The injectable preparation according to any of (180) to (183), wherein it is an analgesic agent.

(188) The tablet according to (184) or (185), wherein it is an analgesic agent.

(189) Use of an extract from inflamed skins of rabbits inoculated with vaccinia virus for the manufacture of a preparation where the variations in the content of sulfated tyrosine among the manufacturing lots are reduced by such a means that, in the manufacture of a preparation containing the extract, the amount of sulfated tyrosine contained in the extract is made 125 ng or more per unit of the extract.

(190) Use of an extract from inflamed skins of rabbits inoculated with vaccinia virus for the manufacture of a preparation containing the extract as an active ingredient where the variations in the content of sulfated tyrosine among the manufacturing lots are reduced so that the amount of sulfated tyrosine contained in the extract is made 125 ng or more per unit of the extract by such a means that, during the steps for the manufacture of the extract, there is conducted a step where an extraction solvent is added to crushed inflamed tissues, allowed to stand for 3 to 7 days and warmed at 30 to 45° C. for 3 to 4 days more.

(191) The use of an extract from inflamed skins of rabbits inoculated with vaccinia virus according to (189) or (190), wherein the content of sulfate sulfated tyrosine is 125 to 425 ng per unit of the extract.

(192) The use of an extract from inflamed skins of rabbits inoculated with vaccinia virus according to (190) or (191), wherein the warming step for 3 to 4 days in the steps of manufacturing the extract is a step of warming at 35 to 40° C. with stirring.

(193) Use of an extract being liquid from inflamed skins of rabbits inoculated with vaccinia virus for the manufacture of a preparation containing the extract as an active ingredient where the variations in the content of sulfated tyrosine among the manufacturing lots are reduced so that the amount of sulfated tyrosine contained in the extract is made 150 ng or more per mL of the extract by such a means that, during the steps for the manufacture of the extract, there is conducted a step where an extraction solvent is added to crushed inflamed tissues, allowed to stand for 3 to 7 days and warmed at 30 to 45° C. for 3 to 4 days more.

(194) The use of an extract being liquid from inflamed skins of rabbits inoculated with vaccinia virus according to (193), wherein the content of sulfated tyrosine is 150 to 510 ng per mL of the extract.

(195) The use of an extract being liquid from inflamed skins of rabbits inoculated with vaccinia virus according to (193) or (194), wherein the warming step for 3 to 4 days in the steps of manufacturing the extract from inflamed skins of rabbits inoculated with vaccinia virus is a step of warming at 35 to 40° C. with stirring.

(196) Use of a preparation as an analgesic agent containing an extract from inflamed skins of rabbits inoculated with vaccinia virus as an active ingredient where the variations in the content of sulfated tyrosine among the manufacturing lots are reduced in the manufacture of the extract by such a means that the amount of sulfated tyrosine contained in the extract is made 125 ng or more per unit of the extract.

(197) Use of a preparation as an analgesic agent containing an extract from inflamed skins of rabbits inoculated with vaccinia virus as an active ingredient where the variations in the content of sulfated tyrosine in the preparation among the manufacturing lots are reduced by such a means that, during the steps for the manufacture of the extract, there is conducted a step where an extraction solvent is added to crushed inflamed tissues, allowed to stand for 3 to 7 days and warmed at 30 to 45° C. for 3 to 4 days more so that the amount of sulfated tyrosine contained in the extract is made 125 ng or more per unit of the extract.

(198) The use of a preparation according to (196) or (197), wherein the content of sulfated tyrosine is 125 to 425 ng per unit of the extract.

(199) The use of a preparation according to (197) or (198), wherein the warming step for 3 to 4 days in the steps of manufacturing the extract from inflamed skins of rabbits inoculated with vaccinia virus is a step of warming at 35 to 40° C. with stirring.

(200) Use of a preparation as an analgesic agent containing an extract being liquid from inflamed skins of rabbits inoculated with vaccinia virus as an active ingredient where the variations in the content of sulfated tyrosine in the preparation among the manufacturing lots are reduced by such a means that, during the steps for the manufacture of the extract, there is conducted a step where an extraction solvent is added to crushed inflamed tissues, allowed to stand for 3 to 7 days and warmed at 30 to 45° C. for 3 to 4 days more so that the amount of sulfated tyrosine contained in the extract is made 150 ng or more per mL of the extract.

(201) The use of a preparation manufactured by using an extract being liquid from inflamed skins of rabbits inoculated with vaccinia virus according to (200), wherein the content of sulfated tyrosine is 150 to 510 ng per mL of the extract.

(202) The use according to (200) or (201), wherein the warming step for 3 to 4 days in the steps for the manufacture of an extract being liquid from inflames skins of rabbits inoculated with vaccinia virus is a step of warming at 35 to 40° C. with stirring.

(203) The use of a preparation according to any of (197) to (202), wherein the preparation is an injectable preparation.

(204) The use of a preparation according to (203), wherein the amount of sulfated tyrosine contained in the injectable preparation is 150 ng or more per mL of the injectable preparation.

(205) The use of a preparation according to (203), wherein the amount of sulfated tyrosine contained in the injectable preparation is 150 to 510 ng per mL of the injectable preparation.

(206) The use of a preparation according to (203), wherein the injectable preparation is a 3 mL injectable preparation and the amount of sulfated tyrosine contained in the injectable preparation is 450 ng or more per ampoule of the injectable preparation.

(207) The use of a preparation according to (203), wherein the injectable preparation is a 3 mL injectable preparation and the amount of sulfated tyrosine contained in the injectable preparation is 450 to 1530 ng per ampoule of the injectable preparation.

(208) The use of a preparation according to any of (197) to (202), wherein the preparation is a tablet.

(209) The use of a preparation according to (208), wherein the amount of sulfated tyrosine contained in the tablet is 500 ng or more per tablet.

(210) The use of a preparation according to (208), wherein the amount of sulfated tyrosine contained in the tablet is 500 to 1700 ng per tablet.

INDUSTRIAL APPLICABILITY

As mentioned hereinabove, the present invention provides an extract from inflamed skins of rabbits inoculated with vaccinia virus or a preparation containing the extract which is deemed to be appropriately manufactured by such a means that the content of sulfated tyrosine is measured so that the fact of containing a predetermined amount therein is confirmed. The present invention also provides an inspection method by which the extract and the preparation is deemed to be appropriately manufactured by means of confirming that each manufacturing lot of the extract contains a predetermined amount of sulfated tyrosine. Since the extract and the preparation as such are manufactured using biological tissues, it is now possible to warrant the quality thereof for each lot in more strictly whereby that is very useful.

The invention claimed is:

1. A preparation comprising an extract from inflamed skins of rabbits inoculated with vaccinia virus, wherein the variations in the effect of the preparation among manufacturing lots are reduced by the amount of sulfated tyrosine contained in the preparation being measured for each manufacturing lot and the content is confirmed to be 125 ng or more per unit of the extract in the preparation.

2. A preparation as claimed in claim 1 which is an injectable preparation and the amount of sulfated tyrosine contained in the injectable preparation is measured for each manufacturing lot and the content is confirmed to be 150 ng or more per mL of the injectable preparation.

3. A preparation as claimed in claim 1 which is a tablet and the amount of sulfated tyrosine contained in the tablet is measured for each manufacturing lot and the content is confirmed to be 500 ng or more per tablet.

4. The preparation according to claim 1, wherein the effect of the preparation is an analgesic effect.

5. An extract from inflamed skins of rabbits inoculated with vaccinia virus, the extract comprising sulfated tyrosine wherein the variations in the content of sulfated tyrosine among the manufacturing lots are reduced so that the amount of sulfated tyrosine contained in the extract is made 125 ng or more per unit of the extract by adding an extraction solvent to crushed inflamed tissues to obtain a mixture, allowing the mixture to stand for 3 to 7 days, and warming the mixture at 30 to 45° C. for 3 to 4 days more.

6. A preparation comprising the extract from inflamed skins of rabbits inoculated with vaccinia virus according to claim 5, wherein the amount of sulfated tyrosine contained in the preparation is 125 ng or more per unit of the extract in the preparation.

7. The preparation according to claim 6, wherein the preparation is an analgesic agent.

8. A method for manufacturing an extract from inflamed skins of rabbits inoculated with vaccinia virus comprising adding an extraction solvent to crushed inflamed tissues to obtain a mixture, and allowing the mixture to stand for 5 to 12 days so that the amount of sulfated tyrosine contained in the extract is made to be 125 ng or more per unit of the extract.

9. The method for manufacturing an extract from inflamed skins of rabbits inoculated with vaccinia virus according to claim 8, wherein warming at 30 to 45° C. with or without stirring is conducted during the period where the extraction solvent is added to crushed inflamed tissues and allowed to stand for 5 to 12 days.

10. The method for manufacturing an extract from inflamed skins of rabbits inoculated with vaccinia virus according to claim 9, wherein, after an extraction solvent is added to the crushed inflamed tissues and allowed to stand for 3 to 7 days, then the resultant extract is warmed at 35 to 40° C. with stirring for 3 to 4 days more.

11. A method for making a preparation containing an extract from inflamed skins of rabbits inoculated with vaccinia virus, comprising providing an extract from inflamed skins of rabbits inoculated with vaccinia virus having a predetermined amount of sulfated tyrosine where the variations in the content of sulfated tyrosine among manufacturing lots are reduced, the amount of sulfated tyrosine contained in the extract being 125 ng or more per unit of the extract, and incorporating the extract into an injectable preparation or a tablet preparation.

12. A method for providing an analgesic effect comprising administering a preparation containing an extract from inflamed skins of rabbits inoculated with vaccinia virus, in which the variations in the analgesic effect of the preparation among manufacturing lots are reduced by the amount of sulfated tyrosine contained in the preparation being measured for each manufacturing lot and the content is confirmed to be 125 ng or more per unit of the extract in the preparation, to a subject in need thereof.

13. A method for controlling the manufacture of a preparation containing an extract from inflamed skins of rabbits inoculated with vaccinia virus in which the variations in the effect of the preparation among manufacturing lots are reduced, comprising measuring the amount of sulfated tyrosine contained in the preparation for each manufacturing lot, and only distributing preparations having a sulfated tyrosine content which is 125 ng or more per unit of the extract in the preparation.

14. A method for controlling the manufacture of a preparation as claimed in claim 13 wherein the preparation is an injectable preparation, and only distributing the preparation when the amount of sulfated tyrosine contained in the injectable preparation is measured for each manufacturing lot and the content is 150 ng or more per mL of the injectable preparation.

15. A method for controlling the manufacture of a preparation as claimed in claim 13 wherein the preparation is a tablet, and only distributing the tablet when the amount of sulfated tyrosine contained in the tablet is measured for each manufacturing lot and the content is 500 ng or more per tablet.

16. The method for controlling the manufacture of a preparation according to claim 13, wherein the effect of the preparation is an analgesic effect.

17. A method for inspection of a preparation containing an extract from inflamed skins of rabbits inoculated with vaccinia virus in which the variations of the effect of the preparation are reduced, comprising measuring the amount of sulfated tyrosine contained in the preparation for each lot, and only shipping, distributing or using preparations as an analgesic which have a sulfated tyrosine content that is 125 ng or more per unit of the extract in the preparation.

18. A method for inspection of a preparation as claimed in claim 17 wherein the preparation is an injectable preparation, and only shipping, distributing or using preparations when the amount of sulfated tyrosine contained in the injectable preparation is measured for each lot and the content is 150 ng or more per mL of the injectable preparation.

19. A method for inspection of a preparation as claimed in claim 17 wherein the preparation is a tablet, and only shipping, distributing or using the tablet when the amount of sulfated tyrosine contained in the tablet is measured for each lot and the content is 500 ng or more per tablet.

20. The method for controlling the manufacture of a preparation according to claim 14 wherein the effect of the preparation is an analgesic effect.

21. The method for controlling the manufacture of a preparation according to claim 15 wherein the effect of the preparation is an analgesic effect.

* * * * *